US010517935B2

(12) United States Patent
Mandler et al.

(10) Patent No.: US 10,517,935 B2
(45) Date of Patent: *Dec. 31, 2019

(54) MIMOTOPES OF ALPHA-SYNUCLEIN AND VACCINES THEREOF FOR THE TREATMENT OF NEURODEGENERATIVE DISORDERS

(71) Applicant: AFFIRIS AG, Vienna (AT)

(72) Inventors: Markus Mandler, Vienna (AT); Harald Weninger, Vienna (AT); Radmila Santic, Vienna (AT); Edith Kopinits, Landegg (AT)

(73) Assignee: AFFIRIS AG, Vienna (AT)

( * ) Notice: Subject to any disclaimer, the term of this patent is extended or adjusted under 35 U.S.C. 154(b) by 0 days.

This patent is subject to a terminal disclaimer.

(21) Appl. No.: 15/375,234

(22) Filed: Dec. 12, 2016

(65) Prior Publication Data

US 2017/0158744 A1    Jun. 8, 2017

Related U.S. Application Data

(63) Continuation of application No. 12/918,077, filed as application No. PCT/AT2009/000071 on Feb. 23, 2009, now Pat. No. 9,724,399.

(30) Foreign Application Priority Data

Feb. 22, 2008   (AT) .................................. A 297/2008

(51) Int. Cl.
*A61K 38/00* (2006.01)
*A61K 49/00* (2006.01)
(Continued)

(52) U.S. Cl.
CPC ........ *A61K 39/0007* (2013.01); *A61K 9/0019* (2013.01); *A61K 38/1709* (2013.01); *A61K 47/02* (2013.01); *A61K 47/643* (2017.08); *C07K 14/47* (2013.01); *C07K 16/4241* (2013.01); *A61K 9/0053* (2013.01); *A61K 31/00* (2013.01); *A61K 38/00* (2013.01); *A61K 39/385* (2013.01); *A61K 39/3955* (2013.01); *A61K 47/42* (2013.01); *A61K 47/6911* (2017.08); *A61K 2039/505* (2013.01); *A61K 2039/55505* (2013.01); *A61K 2039/55516* (2013.01); *A61K 2039/55555* (2013.01); *A61K 2039/55566* (2013.01); *A61K 2039/55572* (2013.01); *A61K 2039/57* (2013.01); *A61K 2039/575* (2013.01); *A61K 2039/58* (2013.01); *A61K 2039/6031* (2013.01); *A61K 2039/6081* (2013.01); *A61K 2039/70* (2013.01); *A61P 25/16* (2018.01); *A61P 25/28* (2018.01); *C07K 7/06* (2013.01); *C07K 7/08* (2013.01); *C07K 16/18* (2013.01);

(Continued)

(58) Field of Classification Search
CPC .... A61K 39/00; A61K 38/00; A61K 2300/00; A61K 2039/55561; A61K 2039/6081; A61K 2039/6056; A61K 47/4833; C07K 2319/00; C07K 2317/34; C07K 16/00; C07K 14/47

See application file for complete search history.

(56) References Cited

U.S. PATENT DOCUMENTS 8,859,628 B2 * 10/2014 McLaurin ............ A61K 31/047
                                                514/729
9,724,399 B2 *  8/2017 Mandler ............ A61K 39/0007
(Continued)

FOREIGN PATENT DOCUMENTS

WO      2004 041067      5/2004
WO      2006 045037      4/2006
WO   WO 2006045037 A2 *  4/2006  ......... A01K 67/0275

OTHER PUBLICATIONS

Jakes, R., et al., "Epitope mapping of LB509, a monoclonal antibody directed against human α-synuclein," Neuroscience Letters, vol. 269, pp. 13-16, (1999).

(Continued)

Primary Examiner — Chang-Yu Wang
(74) Attorney, Agent, or Firm — Oblon, McClelland, Maier & Neustadt, L.L.P.

(57) ABSTRACT

A method of treating a synucleinopathy with a peptide (C)DQPVLPD (SEQ ID NO: 59), (C)DMPVLPD (SEQ ID NO: 60), (C)DSPVLPD (SEQ ID NO: 61), (C)DQPVLPDN (SEQ ID NO: 64), (C)DMPVLPDN (SEQ ID NO: 65), (C)DSPVLPDN (SEQ ID NO: 66), (C)HDRPVTPD (SEQ ID NO: 70), (C)DRPVTPD (SEQ ID NO: 71), (C)DVPVLPD (SEQ ID NO: 72), (C)DTPVYPD (SEQ ID NO: 73), (C)DTPVIPD (SEQ ID NO: 74), (C)HDRPVTPDN (SEQ ID NO: 75), (C)DRPVTPDN (SEQ ID NO: 76), (C)DVPVLPDN (SEQ ID NO: 78), (C)DTPVYPDN (SEQ ID NO: 79), (C)DQPVLPDG (SEQ ID NO: 81), (C)DMPVLPDG (SEQ ID NO: 82), (C)DSPVLPDG (SEQ ID NO: 83), (C)DHPVHPDS (SEQ ID NO: 86), (C)DMPVSPDR (SEQ ID NO: 87), (C)DRPVYPDI (SEQ ID NO: 90), (C)DHPVTPDR (SEQ ID NO: 91), (C)DTPVLPDS (SEQ ID NO: 93), (C)DMPVTPDT (SEQ ID NO: 94), (C)DAPVTPDT (SEQ ID NO: 95), (C)DSPVVPDN (SEQ ID NO: 96), (C)DLPVTPDR (SEQ ID NO: 97), (C)DSPVHPDT (SEQ ID NO: 98), (C)DAPVRPDS (SEQ ID NO: 99), (C)DMPVLPDG (SEQ ID NO: 100), (C)DRPVQPDR (SEQ ID NO: 102), (C)YDRPVQPDR (SEQ ID NO: 103), (C)DMPVDADN (SEQ ID NO: 105), DQPVLPD(C) (SEQ ID NO: 106), and DMPVLPD(C) (SEQ ID NO: 107.

Figure 1:
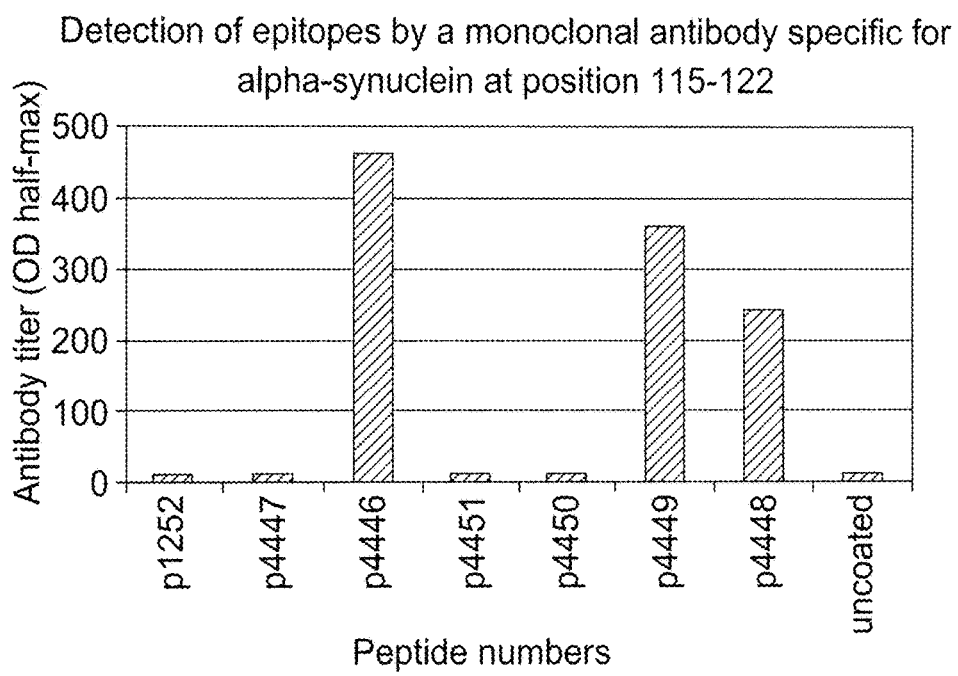
Figure 2:
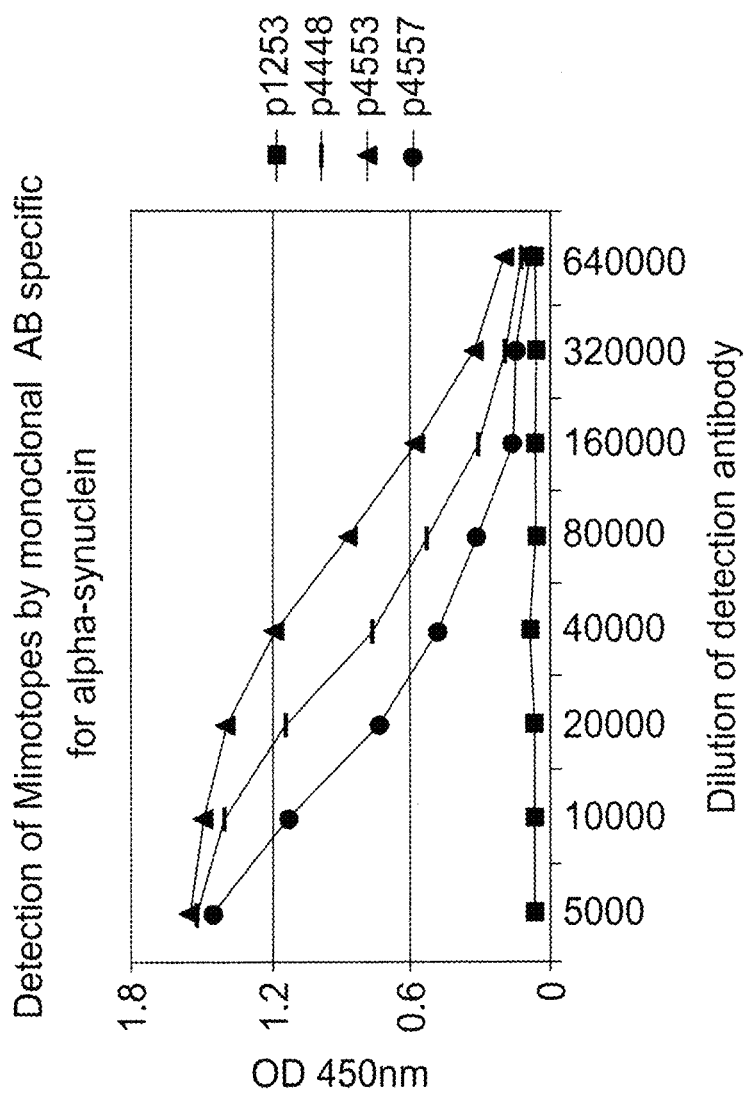
Figure 3:
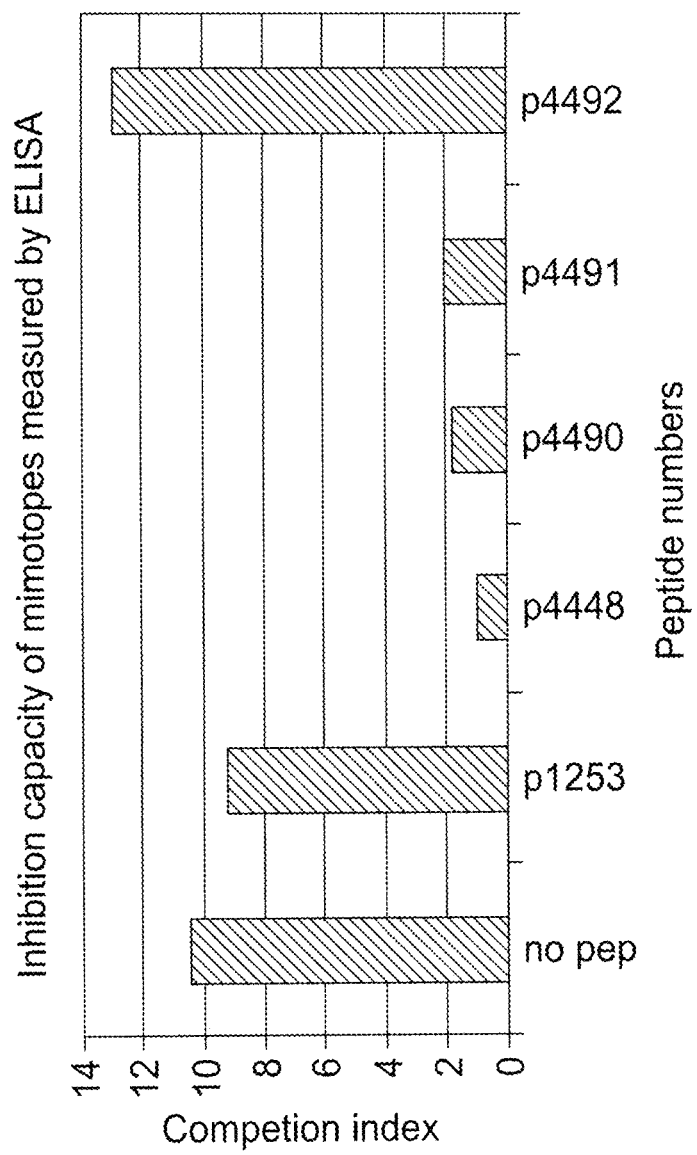

10 Claims, 8 Drawing Sheets
Specification includes a Sequence Listing.

(51) Int. Cl.
| | |
|---|---|
| A61K 38/17 | (2006.01) |
| C07K 14/47 | (2006.01) |
| C07K 14/00 | (2006.01) |
| C07K 4/00 | (2006.01) |
| C07K 5/00 | (2006.01) |
| C07K 7/00 | (2006.01) |
| C07K 2/00 | (2006.01) |
| A61B 5/00 | (2006.01) |
| A61K 39/00 | (2006.01) |
| C07K 16/42 | (2006.01) |
| A61K 9/00 | (2006.01) |
| A61K 47/02 | (2006.01) |
| A61K 47/64 | (2017.01) |
| A61K 39/395 | (2006.01) |
| A61K 39/385 | (2006.01) |
| G01N 33/68 | (2006.01) |
| C07K 16/18 | (2006.01) |
| C07K 7/06 | (2006.01) |
| C07K 7/08 | (2006.01) |
| A61P 25/28 | (2006.01) |
| A61P 25/16 | (2006.01) |
| A61K 31/00 | (2006.01) |
| A61K 47/42 | (2017.01) |
| A61K 47/69 | (2017.01) |

(52) U.S. Cl.
CPC ...... C07K 2317/21 (2013.01); C07K 2317/32 (2013.01); C07K 2317/33 (2013.01); C07K 2317/622 (2013.01); C07K 2317/76 (2013.01); C07K 2319/00 (2013.01); G01N 33/6896 (2013.01); G01N 2800/52 (2013.01)

(56) References Cited

U.S. PATENT DOCUMENTS

| | | | |
|---|---|---|---|
| 2003/0166558 A1 | 9/2003 | Frangione et al. | |
| 2003/0170229 A1 | 9/2003 | Friede et al. | |
| 2005/0198694 A1 | 9/2005 | Chilcote et al. | |
| 2006/0058233 A1* | 3/2006 | Schenk | A61K 38/1709 424/142.1 |
| 2006/0189582 A1* | 8/2006 | McLaurin | A61K 31/045 514/129 |
| 2006/0259986 A1* | 11/2006 | Chilcote | A01K 67/0275 800/3 |
| 2007/0155771 A1* | 7/2007 | Rubinsztein | A61K 31/00 514/291 |
| 2007/0197452 A1* | 8/2007 | McLaurin | A61K 31/045 514/23 |
| 2007/0197453 A1* | 8/2007 | McLaurin | A61K 31/122 514/23 |
| 2007/0213253 A1 | 9/2007 | Sode | |
| 2008/0014194 A1* | 1/2008 | Schenk | C07K 16/18 424/133.1 |
| 2009/0208487 A1* | 8/2009 | Schenk | A61K 39/0007 424/133.1 |
| 2010/0086545 A1* | 4/2010 | Schenk | A61K 39/0007 424/133.1 |
| 2010/0278814 A1* | 11/2010 | Schenk | A61K 39/0007 424/133.1 |
| 2010/0292157 A1* | 11/2010 | Cruz | A61K 31/047 514/17.8 |
| 2012/0142902 A1* | 6/2012 | Schenk | A61K 39/0007 530/387.3 |

OTHER PUBLICATIONS

Iwatsubo, T., "Pathological biochemistry of alpha-synucleinopathy," Neuropathology, vol. 27, No. 5, pp. 474-478, (2007), (Abstract Only).
Office Action dated Dec. 12, 2008, in Austrian Patent Application No. A 297/2008-2, filed Feb. 22, 2008 (with English-language translation).
International Search Report dated Oct. 20, 2009 in PCT/AT09/000071 filed Feb. 23, 2009.
Singleton, Trends in Neuroscience 2005, 28:416-421.
Fleming et al., NeuroRx, 2005. 2: 495-503.
Yu et al. Neuroscience, 2007;p. 145:539-555.
The fact sheet of "Tips for designing a good peptide immunogen" retrieved from the Abcam company's website www.abcan.com/protocols/tips-for - designing-a-good-peptide-immunogen on Aug. 5, 2015.
Giasson et al., J. Neurosci. Res. 2000; 59-528-533.
Howl et al. Methods in Molecular Biology-Peptide Synthesis and Application; Hudecz, Chapter 13: Synthesis of Peptide Bioconjugates, p. 209-223.

* cited by examiner

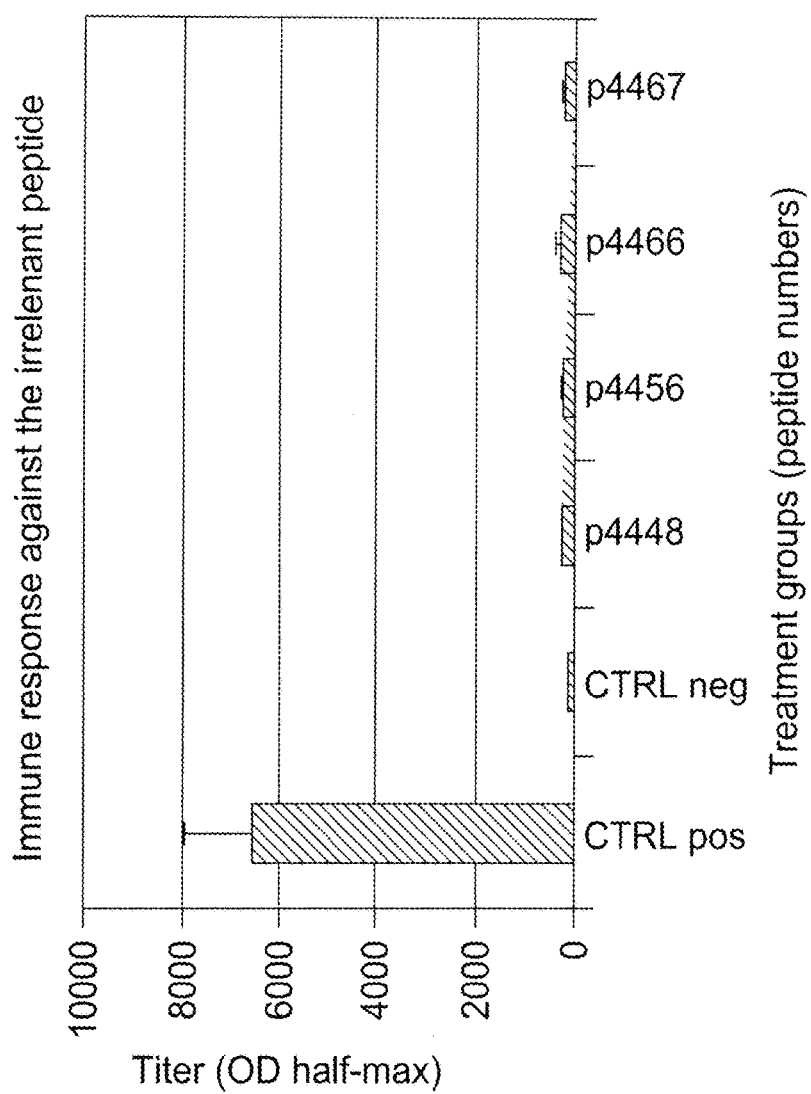

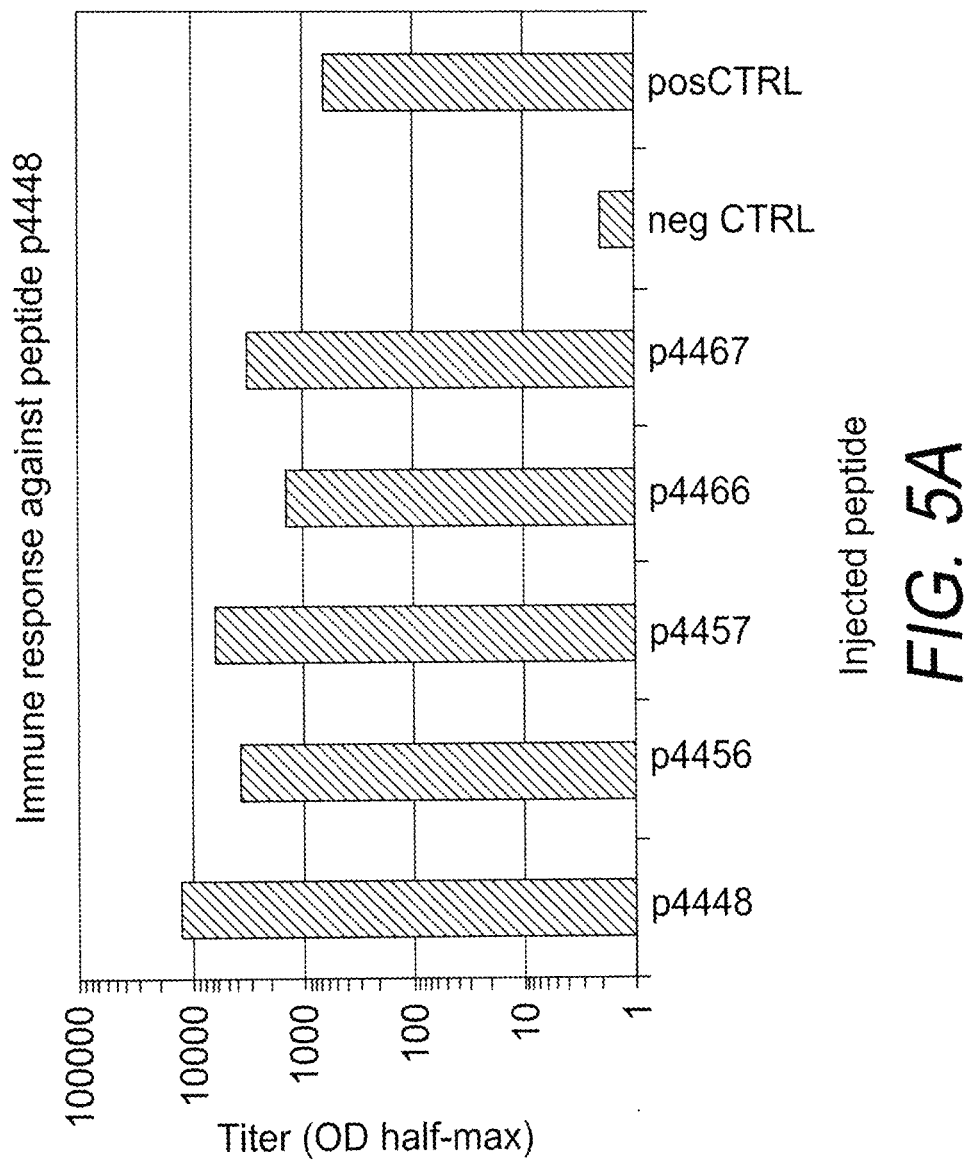

MIMOTOPES OF ALPHA-SYNUCLEIN AND VACCINES THEREOF FOR THE TREATMENT OF NEURODEGENERATIVE DISORDERS

CROSS-REFERENCE TO RELATED APPLICATIONS

The present application is a continuation of U.S. application Ser. No. 12/918,077 filed Aug. 18, 2010, pending, and which is incorporated herein by reference and which is a 35 U.S.C. § 371 National Stage patent application of International patent application PCT/AT2009/000071, filed on Feb. 23, 2009, which claims priority to Austria patent application A297/2008, filed on Feb. 22, 2008.

FIELD OF THE INVENTION

The present invention relates to a medicament to be used to prevent and/or treat synucleinopathies.

BACKGROUND OF THE INVENTION

Synucleinopathies are a diverse group of neurodegenerative disorders that share a common pathologic characteristic: in neuropathologic examinations characteristic lesions can be detected containing abnormal aggregates of alpha-synuclein (alpha-syn) protein in selected populations of neurons and glia cells. Alpha-syn (initially identified as PARK1 and PARK4) is a 140 amino acid protein widely expressed in the neocortex, hippocampus, dentate gyrus, olfactory bulb, striatum, thalamus and cerebellum. Alpha-Syn is also highly expressed in hematopoietic cells including B-, T-, and NK cells as well as monocytes and platelets. The exact role in these cells is not known but it has been implicated in the differentiation of megakaryocytes (platelet precursors).

The most common synucleinopathies include but are not limited to Lewy body disorders (LBDs) like Parkinson's disease (PD), Parkinson's disease with dementia (PDD) and dementia with Lewy bodies (DLB), as well as Multiple System Atrophy (MSA) or Neurodegeneration with Brain Iron Accumulation type I (NBIA Type I). The current treatment options for these diseases include symptomatic medications such as L-dopa, anticholinergic drugs as well as inhibitors of monoamine oxidase. However, all treatment opportunities currently present only lead to symptomatic alleviation but do not induce a long lasting, disease modifying effect in patients.

Lewy body disorders (LBD) are progressive neurodegenerative disorders characterized by tremor, rigidity, bradykinesia and by loss of dopaminergic neurons in the brain. In the case of DLB and PDD signs also include cognitive impairment. Up to 2% of the population above 60 years of age in western countries develop the typical signs of PD/LBD. Currently only symptomatic treatment is available. Unfortunately, these therapies only provide temporary relief from early symptoms and do not halt disease progression.

The pathogenesis of PD/LBD is still incompletely understood, but it appears that genetic susceptibility and environmental factors are involved in the development of the disease. Despite all genetic advances, PD/LBD is primarily a sporadic disorder with no known cause (also called idiopathic PD/LBD). Patients suffering from this disease develop characteristic ubiquitinated intracellular inclusions called Lewy bodies (LBs) in the cortical and subcortical areas of the brain. Especially regions with high content of dopaminergic neurons or neuronal projections show this typical pathologic feature.

Recently, several studies could show that the synaptic protein alpha-syn plays a central role in LBD pathogenesis. In LBD, alpha-syn accumulates in LBs throughout affected brain areas. Additionally, it could be demonstrated that single point mutations as well as duplications or multiplications in the alpha-syn gene are associated with rare familial forms of parkinsonism. Importantly, based on results from overexpression studies in transgenic (tg) mice as well as in *Drosophila melanogaster* its key role in the pathogenesis of PD/LBD is underscored as these animal models mimic several characteristics of PD.

Another very important synucleinopathy is Multiple System Atrophy (MSA). MSA is a sporadic neurodegenerative disorder that is characterised by symptoms of L-DOPA-resistant parkinsonism, cerebellar ataxia, and dysautonomia. Patients suffer from multisystem neuronal loss affecting various brain areas including striatum, substantia nigra, cerebellum, pons, as well as the inferior olives and the spinal cord. MSA is characterized by alpha-syn-positive glial cytoplasmic (GCI) and rare neuronal inclusions throughout the central nervous system. These inclusions are associated with striatonigral degeneration, olivopontocerebellar atrophy, and involvement of autonomic nuclei in medulla and spinal cord. The importance of GCIs for the pathogenesis of MSA is generally acknowledged and underscored by recent analysis of transgenic mouse models analysing the effect of alpha-syn overexpression in oligodendroglia. In tg mice overexpressing human alpha-syn both GCI-like aggregates and biochemical markers of MSA were observed.

Although the exact mechanisms by which accumulation of alpha-syn leads to the typical features of neurodegeneration in synucleopathies and the characteristic symptoms of synucleopathies are not fully understood, recent studies imply that abnormal formation and accumulation of oligomers of alpha-syn are involved in the degenerative processes underlying synucleinopathy. It is currently believed that such oligomer-formation for example in the synaptic terminals and axons plays an important role for PD/LBD development. Hence reduction of alpha-syn deposition and oligomerisation should be beneficial in the treatment of synucleopathies, especially of idiopathic LBD/PD and MSA and could present the first strategy for treatment of these neurodegenerative diseases in addition to the mere alleviation of symptoms resulting from current treatment strategies like L-DOPA application.

In Iwatsubo T. (Neuropathology 27 (5)(2007): 474-478) the correlation of alpha-synuclein depositions as well as its phosphorylation with a pathogenesis of alpha-synucleopathies is examined. The author of this publication found that serine 129 of alpha-synuclein deposited in synucleopathy lesions is extensively phosphorylated.

US 2007/213253 relates to mutant human alpha-synuclein as well as peptides derived therefrom which may be used for inhibiting the aggregation of the wild-type human alpha-synuclein.

In the WO 2004/041067 means and methods for preventing or treating diseases associated with alpha-synuclein aggregation are disclosed which comprise the use of alpha-synuclein fragments.

In the US 2003/166558 peptides are described which can be used to induce immune response to protein deposits.

US 2005/198694 relates to alpha-synuclein fragments comprising at least 100 amino acids and having a C-terminal deletion of 1 to 23 amino acids.

Although experimental therapies utilizing neurotrophic factors and grafting of dopaminergic cells have yielded promising results, alternative approaches designed to reduce the neuronal accumulation of alpha-syn are required.

Recently, active and passive immunotherapy has become of increasing interest as a potential new treatment strategy for neurodegenerative diseases like Alzheimer's disease (AD), Prion Disease, as well as Chorea Huntington and Amyloid Lateral Sclerosis (ALS). For example, recent studies in tg mouse models of AD have shown that antibodies against beta-amyloid 1-42 (Aβ) promote the removal of amyloid from the brain, resulting in improved cognitive performance. Importantly, Aβ molecules are mainly located extracellularly and thus are constituting epitopes accessible to the immune system. In contrast to such 'classical' targets for immunotherapy, experiments have been performed to evaluate the potential of immunotherapy in reducing accumulation of intracellular pathogenic molecules. Vaccination approaches targeting prion protein and huntingtin have been shown to be effective in neurons of tg mice at reducing the accumulation of both molecules that, like alpha-syn, accumulate intracellularly. In addition recent experiments also describe anti-Tau and anti-SOD1 therapies as novel treatment strategies against intracellular pathogenic protein aggregates in AD and ALS respectively. Thus, there is compelling evidence accumulating that intracellular aggregates in brain cells might be targeted by immunotherapy. Indeed, recently a similar potential for the treatment of synucleopathies has been shown. Tg mice overexpressing human alpha-syn were vaccinated with human alpha-syn protein. In mice that produced high relative affinity antibodies upon vaccination, there was decreased accumulation of aggregated alpha-syn in neuronal cell bodies and synapses which was associated with reduced neurodegeneration. Furthermore, antibodies produced by immunized animals also detected abnormal aggregated forms of alpha-syn associated with the neuronal membrane and promoted the degradation of these aggregates, probably via lysosomal pathways. Similar effects were observed using passive immunotherapy with an exogenously applied alpha-syn-specific antibody. These results suggest that vaccination is effective in reducing neuronal accumulation of alpha-syn aggregates and that further development of this approach might elicit beneficial effects in the treatment of LBD and synucleinopathies.

SUMMARY OF THE INVENTION

It is an object of the present invention to provide a medicament to prevent and treat synucleinopathies on the basis of a vaccine.

Therefore the present invention relates to the use of at least one compound comprising the amino acid sequence (Formula 1), $(X_1)_n X_2 X_3 PVX_4 X_5 X_6 (X_7)_m$ (SEQ ID NO: 57)

wherein
$X_1$ is any amino acid residue,
$X_2$ is an amino acid residue selected from the group consisting of aspartic acid (D) and glutamic acid (E),
$X_3$ is any amino acid residue,
$X_4$ is any amino acid residue,
$X_5$ is an amino acid residue selected from the group consisting of proline (P) and alanine (A),
$X_6$ is an amino acid residue selected from the group consisting of aspartic acid (D) and glutamic acid (E),
$X_7$ is any amino acid residue,
n and m, independently, are 0 or an integer of more than 0,
and wherein the amino acid sequence according to Formula I is not identical with, or does not comprise the 8-mer polypeptide fragment of alpha-synuclein having the amino acid sequence DMPVDPDN (SEQ ID NO:1),
said compound having a binding capacity to an antibody which is specific for an epitope of alpha-synuclein comprising the amino acid sequence DMPVDPDN (SEQ ID NO:1) for producing a medicament for preventing and/or treating synucleinopathy.

BRIEF DESCRIPTION OF THE DRAWINGS

The present invention is further illustrated in the following figures and examples, however, without being restricted thereto.

FIG. 1 shows detection of alpha-synuclein specific epitopes by ELISA using a monoclonal specific for human alpha-synuclein at position 115-122.

The peptides p4446 (alpha-synuclein), p4449 and p4448 (human epitopes) are detected by the antibody. The negative control peptides p4447 (beta-synuclein) and p4450, p4451 (mouse epitopes) are not detected. The irrelevant peptide p1252 does not show binding in the ELISA assay. Data are presented in a linear scale.

FIG. 2 shows a detection of mimotopes by ELISA using a monoclonal specific for human alpha-synuclein at position 115-122. Data for two mimotopes (p4553, p4557) are displayed. The peptide p4557 shows weaker binding than the original peptide p4448. The peptide p4553 shows strong binding to the detection antibody. The irrelevant peptide p1253 does not show any binding in the ELISA assay as expected. Both mimotopes induce titers >1/20000 upon vaccination of mice and are considered as strong binders.

FIG. 3 shows detection of competition of mimotopes by ELISA using a monoclonal specific for human alpha-synuclein at position 115-122. Values depicted are measured by ELISA using 40 μg peptide in the inhibition assay. The irrelevant peptide p1253 and the mimotope p4492 do not show competition compared to original peptide p4448. Mimotopes p4490 and p4491 show similar competition as the original peptide p4448. Competition is calculated by comparing OD in ELISA at 40 μg peptide concentration to the original epitope. All mimotopes are compared to this reference resulting in a competition index. Values around 1 indicate high inhibiting capacity. Peptides with a competition index above 5 are rated as non competing.

FIG. 4 shows an immune response against injected peptide and an irrelevant peptide.

A) Sera of immunized mice show high titers against their injected peptides (original epitope (p4448) and mimotopes (p4456, p4466 and p4467 respectively) after 4 vaccinations. Titers measured in ELISA are around 1:10.000 (OD half-max), data are presented in a logarithmic scale. As positive control for the ELISA an alpha-synuclein specific monoclonal antibody was used (CTRL pos).

B) The same sera of immunized mice fail to detect an irrelevant peptide (p1253). Titers measured in ELISA are below 1:100 (OD half-max), more than 100 times lower than a signal from a monoclonal antibody specific for the irrelevant peptide (CTRL pos). As negative control no primary antibody is used. Data are presented in a linear scale.

FIG. 5 shows an immune response against synucleins following repeated mimotope immunizations.

A) Pooled sera of all animals within the respective groups show antibody titers against p4448, a peptide located in the C-terminal part of alpha-synuclein. Data are presented in a logarithmic scale.

B) Pooled sera of immunized mice (p4448, p4457 and p4463) show titers against alpha-synuclein after 4 vaccinations. pooled sera of immunized mice (p4466 and p4467) do not detect alpha nor beta-synuclein (Titers measured in ELISA are much less than 1:100 half-max). Pooled sera of mice immunized with the original epitope (p4448) detect alpha and beta-synuclein. Titers in ELISA, which are less than 1:100 half-max are indicated by an asterisc, corresponding to values close to background. Most of the mimotopes tested induce antibodies that do not cross react with beta-synuclein. Data are presented in a logarithmic scale.

Figure 6B:
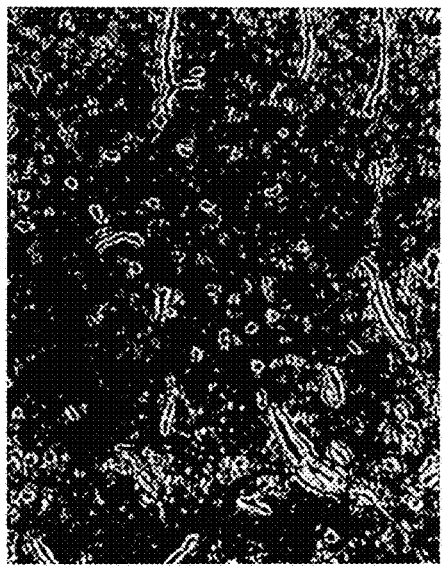
Figure 6C:
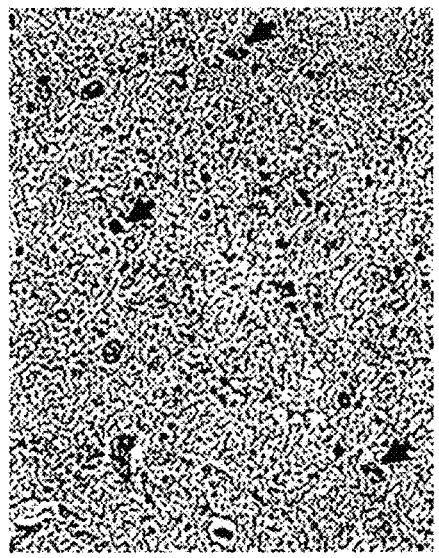
Figure 6A:
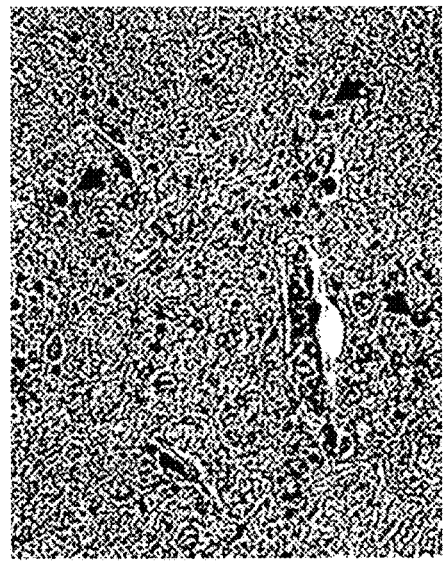

FIG. 6A shows a positive control stain using a commercially available antibody specifically detecting human a-syn. In 6B the same antibody has been used to stain non-transgenic mouse brain of the same area which fails to detect any a-syn positive tissue as this animal is not expressing human a-syn. In 6C a specific a-syn staining similar to the staining present in 6A is elicited by a mimotope induced serum (p4498 induced serum). A-syn positive staining in the murine hippocampus is characterized by the speckled staining patterns as shown in 6A and 6C. Arrows indicate three examples for such a-syn positive inclusions in 6A and 6C respectively.

DETAILED DESCRIPTION OF THE INVENTION

The compounds according to the present invention are able to induce the in vivo formation of antibodies directed (binding) to alpha-synuclein, in particular to the epitope of alpha-synuclein comprising the amino acid sequence DMPVDPDN (SEQI D NO:1) (including also alpha-synuclein fragments comprising said amino acid sequence). Antibodies directed (binding) to said epitope, however, show no or only a significantly lower immune reactivity to beta-synuclein than to alpha-synuclein. In contrast thereto, antibodies induced by immunising with the original alpha-synuclein epitope comprising DMPVDPDN (SEQ ID NO:1) bind surprisingly to both the alpha-synuclein and the beta-synuclein. Therefore, unlike the original alpha-synuclein or fragment(s) thereof, the compounds according to the present invention provide a specificity towards the disease related agent and avoid cross reactivity with disease unrelated beta-synuclein. This strongly suggests significant superiority regarding efficacy and safety, the latter in particular because of the neuroprotective characteristics that have been described for beta-synuclein. Hashimoto M. et al., J Biol Chem. 2004 May 28; 279(22):23622-9. Hashimoto M, Neuron. 2001 Oct. 25; 32(2):213-23.

The alpha-synuclein specific antibodies induced by the administration of the compounds of the present invention might not only bind to monomeric forms of alpha-synuclein but also to multimeric forms. This allows to reduce the amount of oligomers of alpha-synuclein in the body of an individual to be treated. The reduction of alpha-synuclein is particularly beneficial in the treatment of synucleopathies.

The amino acid sequence $(X_1)_n\ X_2X_3PVX_4X_5X_6(X_7)_m$ (SEQ ID NO: 57) is considered to be a mimotope of the epitope of alpha-synuclein comprising the amino acid sequence DMPVDPDN (SEQ ID NO: 1). According to the present invention the term "mimotope" refers to a molecule which has a conformation that has a topology equivalent to the epitope of which it is a mimic. The mimotope binds to the same antigen-binding region of an antibody which binds immunospecifically to a desired antigen. The mimotope will elicit an immunological response in a host that is reactive to the antigen to which it is a mimic. The mimotope may also act as a competitor for the epitope of which it is a mimic in in vitro inhibition assays (e.g. ELISA inhibition assays) which involve the epitope and an antibody binding to said epitope. However, a mimotope of the present invention may not necessarily prevent or compete with the binding of the epitope of which it is a mimic in an in vitro inhibition assay although it is capable to induce a specific immune response when administered to a mammal.

As used herein, the term "epitope" refers to an immunogenic region of an antigen which is recognized by a particular antibody molecule. In general, an antigen will possess one or more epitopes, each capable of binding an antibody that recognizes the particular epitope.

The mimotopes of the present invention can be synthetically produced by chemical synthesis methods which are well known in the art, either as an isolated peptide or as a part of another peptide or polypeptide. Alternatively, the peptide mimotope can be produced in a microorganism which produces the peptide mimotope which is then isolated and if desired, further purified. The peptide mimotope can be produced in microorganisms such as bacteria, yeast or fungi, in eukaryote cells such as a mammalian or an insect cell, or in a recombinant virus vector such as adenovirus, poxvirus, herpesvirus, Simliki forest virus, baculovirus, bacteriophage, sindbis virus or sendai virus. Suitable bacteria for producing the peptide mimotope include *E. coli, B. subtilis* or any other bacterium that is capable of expressing peptides such as the peptide mimotope. Suitable yeast types for expressing the peptide mimotope include *Saccharomyces cerevisiae, Schizosaccharomyces pombe, Candida, Pichia pastoris* or any other yeast capable of expressing peptides. Corresponding methods are well known in the art. Also methods for isolating and purifying recombinantly produced peptides are well known in the art and include e.g. as gel filtration, affinity chromatography, ion exchange chromatography etc.

To facilitate isolation of the peptide mimotope, a fusion polypeptide may be made wherein the peptide mimotope is translationally fused (covalently linked) to a heterologous polypeptide which enables isolation by affinity chromatography. Typical heterologous polypeptides are His-Tag (e.g. $His_6$; 6 histidine residues (SEQ ID NO: 58)), GST-Tag (Glutathione-S-transferase) etc. The fusion polypeptide facilitates not only the purification of the mimotopes but can also prevent the mimotope polypeptide from being degraded during purification. If it is desired to remove the heterologous polypeptide after purification the fusion polypeptide may comprise a cleavage site at the junction between the peptide mimotope and the heterologous polypeptide. The cleavage site consists of an amino acid sequence that is cleaved with an enzyme specific for the amino acid sequence at the site (e.g. proteases).

The mimotopes of the present invention may also be modified at or nearby their N- and/or C-termini so that at said positions a cysteine residue is bound thereto. In a preferred embodiment terminally positioned (located at the N- and C-termini of the peptide) cysteine residues are used to cyclize the peptides through a disulfide bond.

The mimotopes of the present invention may also be used in various assays and kits, in particular in immunological assays and kits. Therefore, it is particularly preferred that the mimotope may be part of another peptide or polypeptide, particularly an enzyme which is used as a reporter in immunological assays. Such reporter enzymes include e.g. alkaline phosphatase or horseradish peroxidase.

The alpha-synuclein mimotopes according to the present invention preferably are antigenic polypeptides which in their amino acid sequence vary from the amino acid sequence of alpha-synuclein or of fragments of alpha-synuclein. In this respect, the inventive mimotopes may not only comprise amino acid substitutions of one or more naturally occurring amino acid residues but also of one or more non-natural amino acids (i.e. not from the 20 "classical" amino acids) or they may be completely assembled of such non-natural amino acids. Moreover, the inventive antigens which induce anti-alpha-synuclein antibodies may be assembled of D- or L-amino acids or of combinations of DL-amino acids and, optionally, they may have been changed by further modifications, ring closures or derivatizations. Suitable antialpha-synuclein-antibody-inducing antigens may be provided from commercially available peptide libraries. Preferably, these peptides are at least 7 amino acids, and preferred lengths may be up to 16, preferably up to 14 or 20 amino acids residues (e.g. 7 or 8 to 20, 7 or 8 to 16 etc.). According to the invention, however, also longer peptides may very well be employed as anti-alpha-synuclein-antibody-inducing antigens. Furthermore the mimotopes of the present invention may also be part of a polypeptide and consequently comprising at their N- and/or C-terminus at least one further amino acid residue.

For preparing alpha-synuclein mimotopes (i.e. anti-alpha-synuclein-antibody-inducing antigens), of course also phage libraries, peptide libraries are suitable, for instance produced by means of combinatorial chemistry or obtained by means of high throughput screening techniques for the most varying structures (Display: A Laboratory Manual by Carlos F. Barbas (Editor), et al.; Willats W G Phage display: practicalities and prospects. Plant Mol. Biol. 2002 December; 50(6):837-54).

Furthermore, according to the invention also anti-alpha-synuclein-antibody-inducing antigens based on nucleic acids ("aptamers") may be employed, and these, too, may be found with the most varying (oligonucleotide) libraries (e.g. with 2-180 nucleic acid residues) (e.g. Burgstaller et al., Curr. Opin. Drug Discov. Dev. 5(5) (2002), 690-700; Famulok et al., Acc. Chem. Res. 33 (2000), 591-599; Mayer et al., PNAS 98 (2001), 4961-4965, etc.). In anti-alpha-synuclein-antibody-inducing antigens based on nucleic acids, the nucleic acid backbone can be provided e.g. by the natural phosphor-diester compounds, or also by phosphorotioates or combinations or chemical variations (e.g. as PNA), wherein as bases, according to the invention primarily U, T, A, C, G, H and mC can be employed. The 2'-residues of the nucleotides which can be used according to the present invention preferably are H, OH, F, Cl, $NH_2$, O-methyl, O-ethyl, O-propyl or O-butyl, wherein the nucleic acids may also be differently modified, i.e. for instance with protective groups, as they are commonly employed in oligonucleotide synthesis. Thus, aptamer-based anti-alpha-synuclein-antibody-inducing antigens are also preferred anti-alpha-synuclein-antibody-inducing antigens within the scope of the present invention.

According to the present invention the term "synucleinopathy" includes all neurodegenerative disorders characterized by pathological synuclein aggregations. Several neurodegenerative disorders including Parkinson's Disease (PD), Lewy Body Disease (LBD), Diffuse Lewy Body Disease (DLBD), Dementia with Lewy Bodies (DLB), Parkinsonism with Dementia (PDD), Multiple System Atrophy (MSA) and Neurodegeneration with Brain Iron Accumulation type I (NBIA Type I) are collectively grouped as synucleinopathies.

The compound according to the present invention may be employed not only for treating synucleinopathies but also to prevent said diseases in individuals being at risk of developing a synucleinopathy (e.g. predisposed, for example genetically predisposed, to developing a synucleinopathy).

The abbreviations for the amino acid residues disclosed in the present invention follow the IUPAC recommendations:

| Amino Acid | 3-Letter Code | 1-Letter Code |
| --- | --- | --- |
| Alanine | Ala | A |
| Arginine | Arg | R |
| Asparagine | Asn | N |
| Aspartic | Asp | D |
| Cysteine | Cys | C |
| Glutamic | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

According to a preferred embodiment of the present invention $X_1$ and/or $X_7$ is an acetylated amino acid residue or cysteine (C).

According to another preferred embodiment of the present invention $X_2$ is glutamine acid, whereby said glutamine acid may also be derivatized to pyroglutamic acid. If $X_2$ comprises a pyroglutamic acid $X_1$ is 0.

According to a further preferred embodiment of the present invention $X_3$ is an amino acid residue selected from the group consisting of glutamine (Q), serine (S), threonine (T), arginine (R), asparagine (N), valine (V), histidine (H), methionine (M), tyrosine (Y), alanine (A) and leucin (L).

According to a preferred embodiment of the present invention $X_4$ is an amino acid residue selected from the group consisting of glutamine (Q), tryptophane (W), threonine (T), arginine (R), aspartic acid(D), isoleucin (I), valine (V), histidine (H), proline (P), tyrosine (Y), alanine (A), serine (S) and leucin (L).

The compound of the present invention may also be part of a polypeptide comprising 7 to 16 amino acid residues. Consequently n and m may independently be an integer selected from the group of 1, 2, 3, 4, 5, 6, 7, 8, 9, 10, 11, 12, 13, 14, 15, 20 and 25.

The compound according to the present invention may consist of the amino acid sequence (X1)nX2X3PVX4X5X6(X7)$_m$ (SEQ ID NO: 57), wherein n and m are independently 0 or 1 or being part of a polypeptide which comprises at least 7 amino acid residues, preferably at least 10 amino acid residues, more preferably at least 15 amino acid residue, and/or a maximum of 50 amino acid residues, preferably a maximum of 30 amino acid residues, more preferably of 16 amino acid residues.

According to a preferred embodiment of the present invention the compound comprises a peptide having an amino acid sequence selected from the group consisting of (C)DQPVLPD (SEQ ID NO: 59), (C)DMPVLPD (SEQ ID NO: 60), (C)DSPVLPD (SEQ ID NO: 61), (C)DSPVWAE (SEQ ID NO: 62), (C)DTPVLAE (SEQ ID NO: 63), (C)DQPVLPDN (SEQ ID NO: 64), (C)DMPVLPDN (SEQ ID NO: 65), (C)DSPVLPDN (SEQ ID NO: 66), (C)DQPVTAEN (SEQ ID NO: 67), (C)DSPVWAEN (SEQ ID NO: 68), (C)DTPVLAEN (SEQ ID NO: 69), (C)HDRPVTPD (SEQ ID NO: 70), (C)DRPVTPD (SEQ ID NO: 71), (C)DVPVLPD (SEQ ID NO: 72), (C)DTPVYPD (SEQ ID NO: 73), (C)DTPVIPD (SEQ ID NO: 74), (C)HDRPVTPDN (SEQ ID NO: 75), (C)DRPVTPDN (SEQ ID NO: 76), (C)DNPVHPEN (SEQ ID NO: 77), (C)DVPVLPDN (SEQ ID NO: 78), (C)DTPVYPDN (SEQ ID NO: 79), (C)DTPVIPDN (SEQ ID NO: 80), (C)DQPVLPDG (SEQ ID NO: 81), (C)DMPVLPDG (SEQ ID NO: 82), (C)DQPVLPDG (SEQ ID NO: 83), (C)DSPVWAEG (SEQ ID NO: 84), (C)DRPVAPEG (SEQ ID NO: 85), (C)DHPVHPDS (SEQ ID NO: 86), (C)DMPVSPDR (SEQ ID NO: 87), (C)DSPVPPDD (SEQ ID NO: 88), (C)DQPVYPDI (SEQ ID NO: 89), (C)DRPVYPDI (SEQ ID NO: 90), (C)DHPVTPDR (SEQ ID NO: 91), (C)EYPVYPES (SEQ ID NO: 92), (C)DTPVLPDS (SEQ ID NO: 93), (C)DMPVTPDT (SEQ ID NO: 94), (C)DAPVTPDT (SEQ ID NO: 95), (C)DSPVVPDN (SEQ ID NO: 96), (C)DLPVTPDR (SEQ ID NO: 97), (C)DSPVHPDT (SEQ ID NO: 98), (C)DAPVRPDS (SEQ ID NO: 99), (C)DMPVWPDG (SEQ ID NO: 100), (C)DAPVYPDG (SEQ ID NO: 101), (C)DRPVQPDR (SEQ ID NO: 102), (C)YDRPVQPDR (SEQ ID NO: 103), (C)DMPVDPEN (SEQ ID NO: 104), (C)DMPVDADN (SEQ ID NO: 105), DQPVLPD(C) (SEQ ID NO: 106), DMPVLPD(C) (SEQ ID NO: 107), (C)EMPVDPDN (SEQ ID NO: 108) and (C)DNPVHPE (SEQ ID NO: 109).

Surprisingly, it turned out that the compounds according to the present invention comprising or consisting of the amino acid sequences listed above are particularly suited to be used for the manufacture of a medicament to be used to treat or prevent synucleinopathies. These peptides (mimotopes) are able to induce the in vivo formation of antibodies directed to the original epitope of human alpha-synuclein comprising the amino acid sequence DMPVDPDN (SEQ ID NO: 1) and human alpha-synuclein protein itself. Said peptides (mimotopes) are, however, not able to induce or only able to induce a very limited immune reactivity against human beta-synuclein protein. Surprisingly, antibodies induced by original alpha-synuclein (comprising the amino acid sequence DMPVDPDN (SEQ ID NO: 1)) are binding to alpha-synuclein as well as beta-synuclein specifically. Thus, said peptides (mimotopes) are inducing a more refined immune response (antibodies) as the original peptide. Mimotope induced immune responses, however, do not necessarily discriminate between alpha-synuclein and beta-synuclein. The peptide induced antibodies are responsible for the removal of alpha-synuclein (which is involved in the formation of alpha-synuclein aggregates, Lewy bodies) and/or for the dissolution of alpha-synuclein aggregates (Lewy bodies) in an individual.

The peptides listed above may comprise at the N-terminus the cystein residue or not, of course the C-residue can also be added to the C-Terminus as well. Therefore, the present invention encompasses the following peptides without the cystein residue at its N-terminus or C-Terminus: DQPVLPD (SEQ ID NO: 110), DMPVLPD (SEQ ID NO: 111), DSPVLPD (SEQ ID NO: 112), DSPVWAE (SEQ ID NO: 113), DTPVLAE (SEQ ID NO: 114), DQPVLPDN (SEQ ID NO: 115), DMPVLPDN (SEQ ID NO: 116), DSPVLPDN (SEQ ID NO: 117), DQPVTAEN (SEQ ID NO: 118), DSPVWAEN (SEQ ID NO: 119), DTPVLAEN (SEQ ID NO: 120), HDRPVTPD (SEQ ID NO: 121), DRPVTPD (SEQ ID NO: 122), DVPVLPD (SEQ ID NO: 123), DTPVYPD (SEQ ID NO: 124), DTPVIPD (SEQ ID NO: 125), HDRPVTPDN (SEQ ID NO: 126), DRPVTPDN (SEQ ID NO: 127), DNPVHPEN (SEQ ID NO: 128), DVPVLPDN (SEQ ID NO: 129), DTPVYPDN (SEQ ID NO: 130), DTPVIPDN (SEQ ID NO: 131), DQPVLPDG (SEQ ID NO: 132), DMPVLPDG (SEQ ID NO: 133), DQPVLPDG (SEQ ID NO: 134), DSPVWAEG (SEQ ID NO: 135), DRPVAPEG (SEQ ID NO: 136), DHPVHPDS (SEQ ID NO: 137), DMPVSPDR (SEQ ID NO: 138), DSPVPPDD (SEQ ID NO: 139), DQPVYPDI (SEQ ID NO: 140), DRPVYPDI (SEQ ID NO: 141), DHPVTPDR (SEQ ID NO: 142), EYPVYPES (SEQ ID NO: 143), DTPVLPDS (SEQ ID NO: 144), DMPVTPDT (SEQ ID NO: 145), DAPVTPDT (SEQ ID NO: 146), DSPVVPDN (SEQ ID NO: 147), DLPVTPDR (SEQ ID NO: 148), DSPVHPDT (SEQ ID NO: 149), DAPVRPDS (SEQ ID NO: 150), DMPVWPDG (SEQ ID NO: 151), DAPVYPDG (SEQ ID NO: 152), DRPVQPDR (SEQ ID NO: 153), YDRPVQPDR (SEQ ID NO: 154), DMPVDPEN (SEQ ID NO: 155), DMPVDADN (SEQ ID NO: 156), EMPVDPDN (SEQ ID NO: 157) and DNPVHPE (SEQ ID NO: 158).

The compound according to the present invention may be used for the preparation of a medicament, in particular a vaccine, which can be used to treat alpha-synucleinopathy, whereby the medicament is particularly suited to treat synucleinopathy selected from the group consisting of Parkinson's Disease (PD), Lewy Body Disease (LBD), Diffuse Lewy Body Disease (DLBD), Dementia with Lewy Bodies (DLB), Parkinsonism with Dementia (PDD), Multiple System Atrophy (MSA) and Neurodegeneration with Brain Iron Accumulation type I (NBIA Type I).

According to a preferred embodiment of the present invention the compound is coupled to a pharmaceutically acceptable carrier, preferably KLH (Keyhole Limpet Hemocyanin), tetanus toxoid, albumin-binding protein, bovine serum albumin, a dendrimer (MAP; Biol. Chem. 358: 581), peptide linkers (or flanking regions) as well as the adjuvant substances described in Singh et al., Nat. Biotech. 17 (1999), 1075-1081 (in particular those in Table 1 of that document), and O'Hagan et al., Nature Reviews, Drug Discovery 2 (9) (2003), 727-735 (in particular the endogenous immunopotentiating compounds and delivery systems described therein), and others or mixtures thereof. The conjugation chemistry (e.g. via heterobifunctional compounds such as GMBS and of course also others as described in "Bioconjugate Techniques", Greg T. Hermanson) in this context can be selected from reactions known to the skilled man in the art. Moreover, the vaccine composition may be formulated with an adjuvant, preferably a low soluble aluminium composition, in particular aluminium hydroxide. Of course, also adjuvants like MF59 aluminium phosphate, calcium phosphate, cytokines (e.g., IL-2, IL-12, GM-CSF), saponins (e.g., QS21), MDP derivatives, CpG oligos, IC31, LPS, MPL, polyphosphazenes, emulsions (e.g., Freund's, SAF), liposomes, virosomes, iscoms, cochleates, PLG microparticles, poloxamer particles, virus-like particles, heat-labile enterotoxin (LT), cholera toxin (CT), mutant toxins (e.g., LTK63 and LTR72), microparticles and/or polymerized liposomes may be used.

The compound of the present invention is preferably bound to the carrier or adjuvant via a linker, which is selected from the group consisting of NHS-poly (ethylene oxide) (PEO) (e.g. NHS -PEO$_4$-maleimide).

A vaccine which comprises the present compound (mimotope) and the pharmaceutically acceptable carrier may be administered by any suitable mode of application, e.g. i.d., i.v., i.p., i.m., intranasally, orally, subcutaneously, etc. and in any suitable delivery device (O'Hagan et al., Nature Reviews, Drug Discovery 2 (9), (2003), 727-735). The compound of the present invention is preferably formulated for intravenous, subcutaneous, intradermal or intramuscular administration (see e.g. "Handbook of Pharmaceutical Manufacturing Formulations", Sarfaraz Niazi, CRC Press Inc, 2004).

Typically, the vaccine contains the compound according to the invention in an amount of from 0.1 ng to 10 mg, preferably 10 ng to 1 mg, in particular 100 ng to 100 µg, or, alternatively, e.g. 100 fmol to 10 µmol, preferably 10 pmol to 1 µmol, in particular 100 pmol to 100 nmol. Typically, the vaccine may also contain auxiliary substances, e.g. buffers, stabilizers etc.

Another aspect of the present invention relates to a peptide having an amino acid sequence selected from the group consisting of (C)DQPVLPD (SEQ ID NO: 59), (C)DMPVLPD (SEQ ID NO: 60), (C)DSPVLPD (SEQ ID NO: 61), (C)DSPVWAE (SEQ ID NO: 62), (C)DTPVLAE (SEQ ID NO: 63), (C)DQPVLPDN (SEQ ID NO: 64), (C)DMPVLPDN (SEQ ID NO: 65), (C)DSPVLPDN (SEQ ID NO: 66), (C)DQPVTAEN (SEQ ID NO: 67), (C)DSPVWAEN (SEQ ID NO: 68), (C)DTPVLAEN (SEQ ID NO: 69), (C)HDRPVTPD (SEQ ID NO: 70), (C)DRPVTPD (SEQ ID NO: 71), (C)DVPVLPD (SEQ ID NO: 72), (C)DTPVYPD (SEQ ID NO: 73), (C)DTPVYPD (SEQ ID NO: 74), (C)HDRPVTPDN (SEQ ID NO: 75), (C)DRPVTPDN (SEQ ID NO: 76), (C)DNPVHPEN (SEQ ID NO: 77), (C)DVPVLPDN (SEQ ID NO: 78), (C)DTPVYPDN (SEQ ID NO: 79), (C)DTPVYPDN (SEQ ID NO: 80), (C)DQPVLPDG (SEQ ID NO: 81), (C)DMPVLPDG (SEQ ID NO: 82), (C)DSPVLPDG (SEQ ID NO: 83), (C)DSPVWAEG (SEQ ID NO: 84), (C)DRPVAPEG (SEQ ID NO: 85), (C)DHPVHPDS (SEQ ID NO: 86), (C)DMPVSPDR (SEQ ID NO: 87), (C)DSPVPPDD (SEQ ID NO: 88), (C)DQPVYPDI (SEQ ID NO: 89), (C)DRPVYPDI (SEQ ID NO: 90), (C)DHPVTPDR (SEQ ID NO: 91), (C)EYPVYPES (SEQ ID NO: 92), (C)DTPVLPDS (SEQ ID NO: 93), (C)DMPVTPDT (SEQ ID NO: 94), (C)DAPVTPDT (SEQ ID NO: 95), (C)DSPVVPDN (SEQ ID NO: 96), (C)DLPVTPDR (SEQ ID NO: 97), (C)DSPVHPDT (SEQ ID NO: 98), (C)DAPVRPDS (SEQ ID NO: 99), (C)DMPVWPDG (SEQ ID NO: 100), (C)DAPVYPDG (SEQ ID NO: 101), (C)DRPVQPDR (SEQ ID NO: 102), (C)YDRPVQPDR (SEQ ID NO: 103), (C)DMPVDPEN (SEQ ID NO: 104), (C)DMPVDADN (SEQ ID NO: 105), DQPVLPD(C) (SEQ ID NO: 106), DMPVLPD(C) (SEQ ID NO: 107), (C)EMPVDPDN (SEQ ID NO: 108) and (C)DNPVHPE (SEQ ID NO: 109). According to a preferred embodiment of the present invention the peptide is coupled to a pharmaceutically acceptable carrier, preferably KLH (Keyhole Limpet Hemocyanin).

Another aspect of the present invention relates to a pharmaceutical formulation, preferably a vaccine, comprising at least one peptide according to the present invention and being selected from the group consisting of (C)DQPVLPD (SEQ ID NO: 59), (C)DMPVLPD (SEQ ID NO: 60), (C)DSPVLPD (SEQ ID NO: 61), (C)DSPVWAE (SEQ ID NO: 62), (C)DTPVLAE (SEQ ID NO: 63), (C)DQPVLPDN (SEQ ID NO: 64), (C)DMPVLPDN (SEQ ID NO: 65), (C)DSPVLPDN (SEQ ID NO: 66), (C)DQPVTAEN (SEQ ID NO: 67), (C)DSPVWAEN (SEQ ID NO: 68), (C)DTPVLAEN (SEQ ID NO: 69), (C)HDRPVTPD (SEQ ID NO: 70), (C)DRPVTPD (SEQ ID NO: 71), (C)DVPVLPD (SEQ ID NO: 72), (C)DTPVYPD (SEQ ID NO: 73), (C)DTPVYPD (SEQ ID NO: 74), (C)HDRPVTPDN (SEQ ID NO: 75), (C)DRPVTPDN (SEQ ID NO: 76), (C)DNPVHPEN (SEQ ID NO: 77), (C)DVPVLPDN (SEQ ID NO: 78), (C)DTPVYPDN (SEQ ID NO: 79), (C)DTPVIPDN (SEQ ID NO: 80), (C)DQPVLPDG (SEQ ID NO: 81), (C)DMPVLPDG (SEQ ID NO: 82), (C)DSPVLPDG (SEQ ID NO: 83), (C)DSPVWAEG (SEQ ID NO: 84), (C)DRPVAPEG (SEQ ID NO: 85), (C)DHPVHPDS (SEQ ID NO: 86), (C)DMPVSPDR (SEQ ID NO: 87), (C)DSPVPPDD (SEQ ID NO: 88), (C)DQPVYPDI (SEQ ID NO: 89), (C)DRPVYPDI (SEQ ID NO: 90), (C)DHPVTPDR (SEQ ID NO: 91), (C)EYPVYPES (SEQ ID NO: 92), (C)DTPVLPDS (SEQ ID NO: 93), (C)DMPVTPDT (SEQ ID NO: 94), (C)DAPVTPDT (SEQ ID NO: 95), (C)DSPVVPDN (SEQ ID NO: 96), (C)DLPVTPDR (SEQ ID NO: 97), (C)DSPVHPDT (SEQ ID NO: 98), (C)DAPVRPDS (SEQ ID NO: 99), (C)DMPVLPDG (SEQ ID NO: 100), (C)DAPVYPDG (SEQ ID NO: 101), (C)DRPVQPDR (SEQ ID NO: 102), (C)YDRPVQPDR (SEQ ID NO: 103), (C)DMPVDPEN (SEQ ID NO: 104), (C)DMPVDADN (SEQ ID NO: 105), DQPVLPD(C) (SEQ ID NO: 106), DMPVLPD(C) (SEQ ID NO: 107), (C)EMPVDPDN (SEQ ID NO: 108) and (C)DNPVHPE (SEQ ID NO: 109).

The pharmaceutical formulation according to the present invention, which can be formulated as a vaccine for, e.g., subcutaneous, intravenous and/or intramuscular administration, may be used in the treatment of any kind of synucleinopathy.

EXAMPLES

An antibody which may be used for the mimotope identification according to the present invention detects the human alpha-synuclein-derived amino acid sequence DMPVDPDN(=original epitope, SEQ ID No. 1) and full length human alpha-synuclein. It does not recognize human beta-synuclein. The antibody may be a monoclonal or polyclonal antibody preparation or any antibody part or derivative thereof and binds specifically to the DMPVDPDN epitope (SEQ ID NO: 1) of human alpha-synuclein, i. e. it does bind to peptide and full length protein but does not bind to human beta-synuclein.

The mimotopes are identified and further characterised with such monoclonal antibodies (detecting a sequence within amino acids 115-122 of the human alpha-synuclein protein) and peptide libraries.

Example 1

Generation of Monoclonal Antibodies to Specifically Detect Original Human Alpha-Synuclein Epitope C-DMPVDPDN (SEQ ID NO: 159) and Human Alpha-Synuclein but not Human Beta-Synuclein A monoclonal antibody derived from the fusion "AFFiRiS 3": Balb/c mice were immunized with original alpha-synuclein epitope C-DMPVDPDN (SEQ ID NO: 159) coupled to BTG (bovine Thyroglobulin) and CFA (complete Freund's adjuvant; first injection) as well as IFA (incomplete Freund's adjuvant; 3 booster injections) as adjuvant. DMPVDPDN-peptide-specific ('DMPVDPDN' disclosed as SEQ ID NO: 1), antibody-producing hybridomas are detected by ELISA (DMPVDPDN-peptide-coated ELISA plates ('DMPVDPDN' disclosed as SEQ ID NO: 1)). Human alpha-synuclein (recombinant protein) is used as positive control peptide: hybridomas recognizing the recombinant protein immobilised on ELISA plates are included because they are binding both peptide and full length alpha-synuclein specifically. Human beta-synuclein (recombinant protein) is used as negative control peptide: hybridomas recognizing both recombinant proteins immobilised on ELISA plates are excluded because they do not distinguish between the two different synuclein proteins.

The Hybridoma clone (AFFiRiS3/9 (internal name "A509"; IgG1) was analysed for specific detection of the natural human alpha-synuclein epitope DMPVDPDN (SEQ ID NO: 1). A509 recognizes the injected epitope as well as full length alpha-synuclein protein (recombinant protein; obtained from rPeptide, Bogart, Ga., USA) in ELISA. It however does not detect beta-synuclein protein (recombinant protein, obtained from rPeptide, Bogart, Ga., USA) in ELISA. Furthermore, the A509 antibodies do not detect the peptide encoding the mouse variant of alpha-synuclein. Similar results can be obtained with commercially available mAB clones (i.e. alpha-synuclein (LB509) Monoclonal Antibody Catalog Number SIG-39725; Covance (Princton, N.J., USA)).

Example 2

Phage Display, In Vitro Binding and Inhibition ELISA

Phage Display libraries used in this example were: Ph.D. 7: New England BioLabs E8102L (linear 7mer library) and Ph.D. 12: New England BioLabs E8111L (linear 12mer library) Phage Display was done according to manufacturer's protocol.

After 2 or 3 subsequent rounds of panning, single phage clones were picked and phage supernatants were subjected to ELISA on plates coated with the antibody that was used for the panning procedure. Phage clones that were positive in this ELISA (strong signal for the target, but no signal for unspecific control) were sequenced. From DNA sequences, peptide sequences were deduced. These peptides were synthesized and characterised in binding and inhibition ELISA. To some peptides additional AA were attached to the C-terminus. Additionally, some novel mimotopes were created by combining sequence information from mimotopes identified in the screen. Both groups containing newly designed mimotopes were used to support the identification of a consensus sequence for a mimotope vaccination.

1. In Vitro Binding Assay (ELISA)

Peptides derived from Phage Display as well as C-terminally prolonged variants thereof were coupled to BSA and bound to ELISA plates (1 µM; as indicated in the respective figures) and subsequently incubated with the monoclonal antibody that was used for the screening procedure to analyse binding capacity of identified peptides.

2. In Vitro Inhibition Assay (ELISA)

Different amounts of peptides (concentrations ranging from 40 µg to 0.3 µg (serial dilutions), as indicated in the respective figures) derived from Phage Display were incubated with the monoclonal antibody that was used for the screening procedure. Peptides diminishing subsequent binding of the antibody to the original human alpha-synuclein epitope (amino acids: 115-122 of human alpha-synuclein protein) coated on ELISA plates were considered as inhibiting in this assay.

Example 3

In Vivo Testing of Mimotopes: Analysis of Immuno-Genicity and Crossreactivity

1. In Vivo Testing of Mimotopes

Figure 4A:
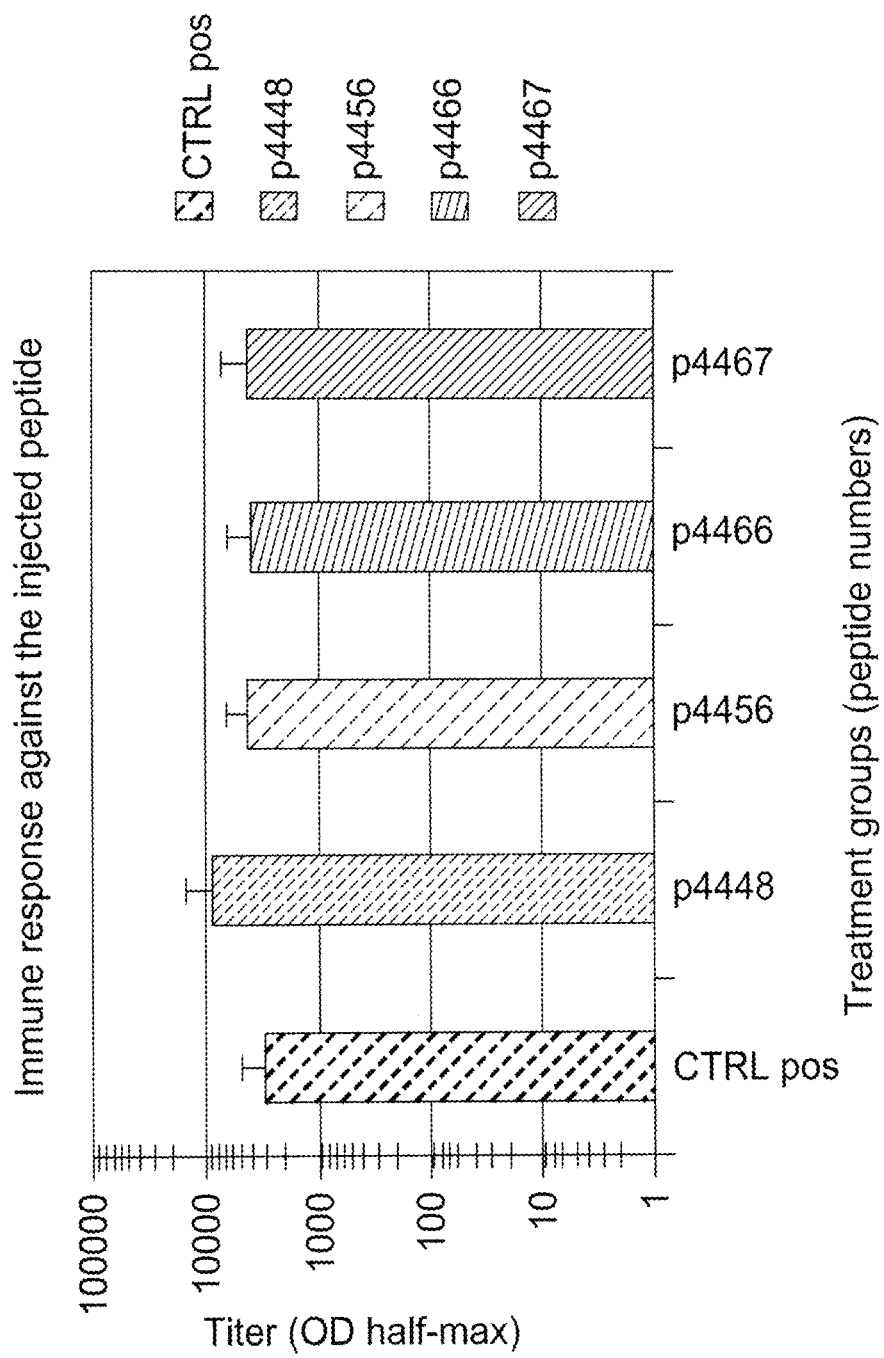
Figure 5B:
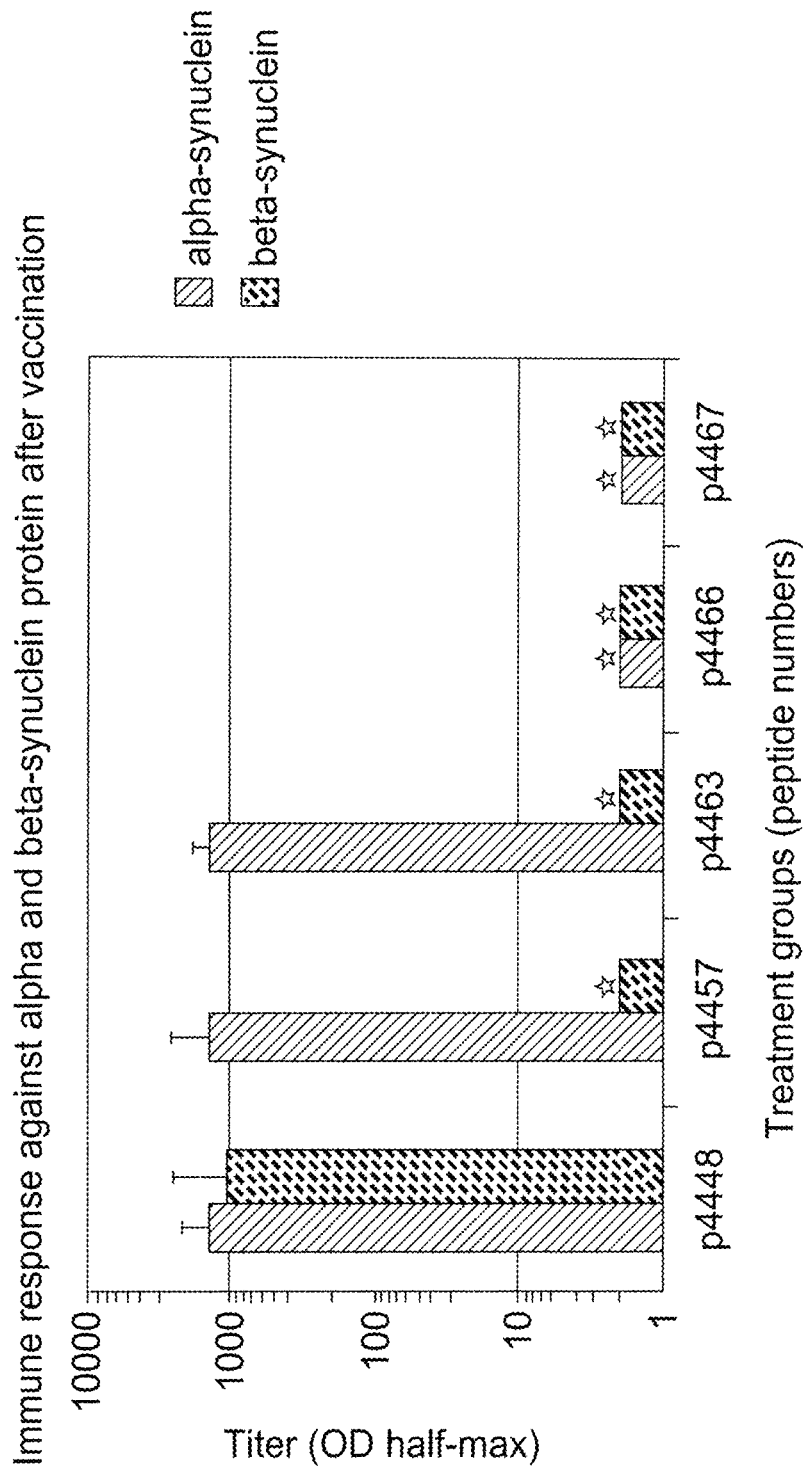

Inhibiting as well as non-inhibiting peptides were coupled to KLH and injected into mice (wildtype C57/Bl6 mice; subcutaneous injection into the flank) together with an appropriate adjuvant (aluminium hydroxide). Animals were vaccinated 4-6 times in biweekly intervals and sera were taken biweekly as well. Titers to injected peptides as well as to an irrelevant peptide were determined with every serum. Titers against the recombinant human alpha-synuclein protein and recombinant human beta-synuclein were determined starting with Serum 3 respectively. Pooled sera were tested against the original human alpha-synuclein epitope (aa115-122). In general sera were analysed by reaction against peptides coupled to Bovine Serum Albumin (BSA) and recombinant full length proteins which were immobilised on ELISA plates. Titers were determined using anti mouse IgG specific antibodies. For detailed results see FIGS. 4 and 5.

2. In Situ Testing of Mimotopes

Selected sera eliciting an a-syn cross reactivity were also tested for the ability to detect human a-syn on mouse brain sections in situ. For detailed results see FIG. 6.

3. Results 3.1. Identification of an Alpha-Synuclein Specific mAB:

FIG. 1 depicts the characterisation of the alpha-synuclein specific monoclonal antibody AFFiRiS3/9 (internal name "A509"; IgG1) derived from fusion AFFiRiS 3.

3.2. Screening with Alpha-Synuclein Specific mAB:

3.2.1. Phage Display Library pH.D. 7 and 12

3.2.1.1. Screening with Monoclonal Antibody Directed Against DMPVDPDN (SEQ ID NO: 1)

51 sequences were identified by screening PhD 7 and PhD12 phage display libraries in this screen: Table 1 summarises the peptides identified and their binding capacity as compared to the original epitope.

TABLE 1 alpha-synuclein mimotopes binding to the parental antibody

| Internal Peptide number | SEQ ID No. | Sequence | Binding Capacity |
|---|---|---|---|
| p4456 | 2 | CDQPVLPD | 3 |
| p4457 | 3 | CDMPVLPD | 3 |
| p4458 | 4 | CDSPVLPD | 3 |
| p4460 | 5 | CDSPVWAE | 1 |
| p4461 | 6 | CDTPVLAE | 1 |
| p4462 | 7 | CDQPVLPDN | 3 |
| p4463 | 8 | CDMPVLPDN | 3 |
| p4464 | 9 | CDSPVLPDN | 3 |
| p4465 | 10 | CDQPVTAEN | 3 |
| p4466 | 11 | CDSPVWAEN | 3 |
| p4467 | 12 | CDTPVLAEN | 3 |
| p4484 | 13 | CHDRPVTPD | 3 |
| p4485 | 14 | CDRPVTPD | 3 |
| P4486 | 15 | CDNPVHPE | 1 |
| p4487 | 16 | CDVPVLPD | 3 |

TABLE 1-continued alpha-synuclein mimotopes binding to the parental antibody

| Internal Peptide number | SEQ ID No. | Sequence | Binding Capacity |
|---|---|---|---|
| p4488 | 17 | CDTPVYPD | 3 |
| p4489 | 18 | CDTPVIPD | 3 |
| p4490 | 19 | CHDRPVTPDN | 3 |
| p4491 | 20 | CDRPVTPDN | 3 |
| p4492 | 21 | CDNPVHPEN | 3 |
| p4493 | 22 | CDVPVLPDN | 3 |
| p4494 | 23 | CDTPVYPDN | 3 |
| p4495 | 24 | CDTPVIPDN | 3 |
| p4496 | 25 | CDQPVLPDG | 3 |
| p4497 | 26 | CDMPVLPDG | 3 |
| p4498 | 27 | CDSPVLPDG | 3 |
| p4499 | 28 | CDSPVWAEG | 3 |
| p4553 | 29 | CDRPVAPEG | 3 |
| p4554 | 30 | CDHPVHPDS | 3 |
| p4555 | 31 | CDMPVSPDR | 3 |
| p4556 | 32 | CDSPVPPDD | 3 |
| p4557 | 33 | CDQPVYPDI | 3 |
| p4558 | 34 | CDRPVYPDI | 3 |
| p4559 | 35 | CDHPVTPDR | 1 |
| p4560 | 36 | CEYPVYPES | 3 |
| p4561 | 37 | CDTPVLPDS | 3 |
| p4562 | 38 | CDMPVTPDT | 3 |
| p4563 | 39 | CDAPVTPDT | 3 |
| p4564 | 40 | CDSPVVPDN | 3 |
| p4566 | 41 | CDLPVTPDR | 3 |
| p4567 | 42 | CDSPVHPDT | 3 |
| p4568 | 43 | CDAPVRPDS | 3 |
| p4569 | 44 | CDMPVWPDG | 3 |
| p4570 | 45 | CDAPVYPDG | 3 |
| p4571 | 46 | CDRPVQPDR | 3 |
| p4572 | 47 | CYDRPVQPDR | 3 |
| p4635 | 48 | CDMPVDPEN | 3 |
| p4636 | 49 | CDMPVDADN | 3 |
| p4640 | 50 | DQPVLPDC | 3 |
| p4641 | 51 | DMPVLPDC | 3 |
| P4648 | 52 | CEMPVDPDN | 3 |

Legend to Table 1: the binding capacity is coded by the following binding code: 1:X describes the dilution factor of the parental AB.

| binding code | | OD halfmax 1:X |
|---|---|---|
| 0 | no binding | :0 |
| 1 | weak binding | :<5000 |
| 2 | medium binding | :5000-20000 |
| 3 | binding as original epitope (strong binding) | :20000-128000 |

3.3. In Vitro Characterisation of Mimotopes Identified in Screening Phage Display Libraries with a Monoclonal Antibody Directed Against Alpha-Synuclein:

FIGS. 2 and 3 show representative examples for binding and inhibition assays used to characterise mimotopes in vitro. Data obtained are summarised in Tables 1 and 2 respectively.

From the 51 sequences presented 29 sequences inhibit binding of the alpha-synuclein specific monoclonal antibody in in vitro competition experiments: Additional 22 sequences were identified that do not inhibit binding of monoclonal antibody in in vitro competition experiments but still retain binding capacity to the parental antibody:

TABLE 2

| Alpha-synuclein mimotopes identified in this invention giving positive results in inhibition assays | | | |
|---|---|---|---|
| Internal Peptide number | SEQ ID No. | Sequence | Inhibition |
| p4462 | 7 | CDQPVLPDN | 2 |
| p4463 | 8 | CDMPVLPDN | 2 |
| p4464 | 9 | CDSPVLPDN | 2 |
| p4490 | 19 | CHDRPVTPDN | 2 |
| p4491 | 20 | CDRPVTPDN | 1 |
| p4493 | 22 | CDVPVLPDN | 2 |
| p4494 | 23 | CDTPVYPDN | 2 |
| p4495 | 24 | CDTPVIPDN | 1 |
| p4496 | 25 | CDQPVLPDG | 1 |
| P4497 | 26 | CDMPVLPDG | 1 |
| p4498 | 27 | CDSPVLPDG | 1 |
| p4554 | 30 | CDHPVHPDS | 1 |
| p4555 | 31 | CDMPVSPDR | 1 |
| p4557 | 33 | CDQPVYPDI | 1 |
| p4558 | 34 | CDRPVYPDI | 2 |
| p4559 | 35 | CDHPVTPDR | 1 |
| p4561 | 37 | CDTPVLPDS | 2 |
| p4562 | 38 | CDMPVTPDT | 2 |
| p4563 | 39 | CDAPVTPDT | 1 |

TABLE 2-continued Alpha-synuclein mimotopes identified in this invention giving positive results in inhibition assays

| Internal Peptide number | SEQ ID No. | Sequence | Inhibition |
|---|---|---|---|
| p4564 | 40 | CDSPVVPDN | 1 |
| p4566 | 41 | CDLPVTPDR | 1 |
| p4567 | 42 | CDSPVHPDT | 1 |
| p4569 | 44 | CDMPVWPDG | 1 |
| p4570 | 45 | CDAPVYPDG | 1 |
| p4571 | 46 | CDRPVQPDR | 1 |
| p4572 | 47 | CYDRPVQPDR | 1 |
| p4640 | 50 | DQPVLPDC | 2 |
| P4641 | 51 | DMPVLPDC | 2 |
| P4648 | 52 | CEMPVDPDN | 1 |

Legend to Table 2: the inhibition capacity is coded by the following code:

Weak inhibition means more peptide is required to lower AB binding than with the original epitope; strong inhibition means similar peptide amounts are required for mimotope and original epitope for lowering AB binding. Mimotopes are compared to the original peptide as standard. OD at 40 µg peptide used in the assay is used to calculate the competition capacity compared to original peptide.

| competition code | |
|---|---|
| 0 | no inhibition (OD of 40 µg peptide above 5 times of original peptide) |
| 1 | Weaker than original epitope (OD of 40 µg peptide below 5 times of original peptide) |
| 2 | strong inhibition (as original epitope; OD of 40 µg peptide below 2 times of original peptide) |

TABLE 3

Non-Mimotope peptides and proteins:

| Internal Peptide number | SEQ ID No. | Sequence |
|---|---|---|
|  | 1 | DMPVDPDN |
| p4446 |  | Human alpha-syn (Full-length; NCBI Acc. No. NP_000336) |
| p4447 |  | Human beta-syn (Full-length; NCBI Acc. No. NP_001001502) |
| p4448 | 53 | CDMPVDPDN |
| p4449 | 54 | DMPVDPDNC |
| p4450 | 55 | CDMPVDPGS |
| p4451 | 56 | DMPVDPGSC |

3.4. In Vivo Characterisation of Mimotopes Identified in Screening Phage Display Libraries with a Monoclonal Antibody Directed Against Alpha-Synuclein:

Female C57/Bl6 mice, 5-6 mice per group, were subcutaneously immunized with 30 µg peptide coupled to KLH. Control groups were administered p4448-KLH conjugate. As adjuvant alum was used (always 1 mg per mouse). The peptides administered were all able to bind to monoclonal antibodies specifically binding aa115-122 of human alpha-synuclein although some of the peptides did not inhibit the binding of the original epitope to its parental antibody in vitro (in an in vitro inhibition assay). The in vitro ELISA assay to determine the antibody titer was performed with sera of single mice or pooled sera (see FIG. 5) after each vaccination in a two week interval (see FIGS. 4 and 5, respectively). The wells of the ELISA plate were coated with mimotope-BSA conjugate and an irrelevant peptide-BSA conjugate (negative control). The positive control was performed by reaction of the parental antibody with the respective mimotope-BSA conjugate. The detection was performed with anti-mouse IgG. Additionally, recombinant proteins were immobilised on ELISA plates and sera reacted accordingly.

For all mimotopes tested in C57/Bl6 mice, antibodies reacting to the individual injected peptide could be detected after repeated vaccination. Additionally, 2 out of 4 depicted mimotopes (see FIG. 5 and Table 1 respectively) developed antibodies reacting with human alpha-synuclein but not with human beta-synuclein. 2/4 showed no cross reactivity with recombinant proteins. Importantly, the original epitope DMPVDPDN (SEQ ID NO: 1) led to an immune response which did not distinguish between the two recombinant synuclein proteins.

FIGS. 4 and 5 show representative examples for assays used to characterise mimotopes in vivo. FIG. 4 shows an example for in vivo characterisations of the immune response elicited by mimotope vaccination by analysing the immune response against injected peptide and an irrelevant peptide, containing an unrelated sequence. The original epitope p4448, the positive control peptide, and the mimotopes p4456, p4466 and p4467, elicited immune responses against the injected peptide (themselves) but failed to induce an unspecific immune response against an unrelated sequence (p1253).

FIG. 5 shows an example for in vivo characterisations of the immune response elicited by mimotope vaccination against full length alpha-synuclein and beta-synuclein. All vaccines tested in this example mounted a detectable immune response against the original alpha-synuclein epitope 115-122. Nearly all mimotopes and the original epitope tested in this example (exception: p4466 and p4467) furthermore also show reactivity with full length alpha-synuclein. However, the original epitope-induced immune response also detected the full length beta-synuclein protein thus loosing the specificity for alpha-synuclein and the ability to distinguish between the two proteins. In contrast to this finding most of (but not all) the mimotope-induced sera failed to detect beta-synuclein thus preserving the ability to discriminate between the two synuclein proteins and guaranteeing high anti alpha-synuclein specificity of an active immunisation programme, to obtain efficacy and an excellent safety profile.

3.5. In Situ Testing of Mimotopes

Mimotopes eliciting an a-syn specific immune response can also detect a-syn immunoreactive inclusions in transgenic mouse brain tissue. As depicted in FIG. 6, sera derived from mimotope vaccinated animals are able to stain a-syn positive structures present on mouse brain sections from animals overexpressing human a-syn. Briefly, sera positive for human a-syn reactivity in ELISA have been used for immunohistochemistry (IHC). Paraffin embedded 7 µM sections of mouse brain, mounted on Superfrost Plus glass slides, were subjected to IHC. Sections were incubated with sera (dilution 1:100 and 1:400 in PBS) and subsequently stained according to standard protocols for immunohistochemistry using VECTASTAIN™ ABC Systems(which is an Avidin-Biotin Complex Immunohistochemical Staining Kit from Vector Laboratories), DAB and MOM blocking (all reactions have been performed using commercially available reagents obtained from Vector labs respectively and have been performed according to manufacturer's protocols). Counterstaining was performed with Haematoxylin. Slides were mounted in Entellan and subsequently documented using conventional brightfield microscopy. A monoclonal antibody specific for human a-syn (LB509, Covance) has been used as a positive control for synuclein detection at a final dilution of 1/250.

In FIG. 6A a positive control stain is depicted. In 6B the same antibody has been used on non-transgenic mouse brain of the same area which failed to detect any a-syn positive tissue as this animal is not expressing human a-syn. In 6C a specific a-syn staining similar to the staining present in 6A is elicited by a mimotope induced serum (p4498 induced serum). A-syn positive staining in the murine hippocampus is characterized by the speckled staining patterns as shown in 6A and 6C. Examples for the potential to induce a-syn specific antibodies include but are not limited to vaccines based on p4456, p4498 and p4562 respectively.

The invention claimed is:

1. A method of reducing aggregates of α-synuclein in a subject having a disease selected from the group consisting of Lewy Body Disorder, Parkinson's Disease, Parkinson's Disease with Dementia, Dementia with Lewy Bodies, Multiple System Atrophy, and Neurodegeneration with Brain Iron Accumulation type I, comprising administering, to a subject in need thereof, a composition comprising a compound comprising a peptide that can induce in vivo formation of antibodies specifically binding to α-synuclein, the peptide having the amino acid sequence selected from the group consisting of SEQ ID NO: 60, SEQ ID NO: 61, SEQ ID NO: 64, SEQ ID NO: 65, SEQ ID NO: 66, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 78, SEQ ID NO: 79, SEQ ID NO: 81, SEQ ID NO: 82, SEQ ID NO: 83, SEQ ID NO: 86, SEQ ID NO: 87, SEQ ID NO: 90, SEQ ID NO: 91, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 102, SEQ ID NO: 103, SEQ ID NO: 105, SEQ ID NO: 106, and SEQ ID NO: 107.

2. The method of claim 1, wherein the peptide is the amino acid sequence of SEQ ID NO:64, SEQ ID NO:81, or SEQ ID NO: 106.

3. The method of claim 1, wherein the peptide comprises an acetylated amino acid residue or a cysteine at an N-terminus, a C-terminus or both an N- terminus and C-terminus of the peptide.

4. The method of claim 1, wherein the compound is coupled to a pharmaceutically acceptable carrier that is keyhole limpet hemocyanin.

5. The method of claim 1, wherein the composition is formulated for and administered intravenously, subcutaneously, intradermally, or intramuscularly.

6. The method of claim 1, wherein the composition further comprises an adjuvant.

7. The method of claim 6, wherein the adjuvant is aluminium hydroxide.

8. The method of claim 1, wherein the composition comprises from 0.1 ng to 10 mg of the compound.

9. The method of claim 1, wherein the composition comprises from 10 ng to 1 mg of the compound.

10. The method of claim 1, wherein the composition comprises from 100 ng to 100 μg of the compound.

* * * * *

SEQUENCE LISTING

```
<160> NUMBER OF SEQ ID NOS: 159

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Asp Met Pro Val Asp Pro Asp Asn
1               5

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Cys Asp Gln Pro Val Leu Pro Asp
1               5

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Cys Asp Met Pro Val Leu Pro Asp
1               5

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Cys Asp Ser Pro Val Leu Pro Asp
1               5
```

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Cys Asp Ser Pro Val Trp Ala Glu
1               5

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Cys Asp Thr Pro Val Leu Ala Glu
1               5

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Cys Asp Gln Pro Val Leu Pro Asp Asn
1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Cys Asp Met Pro Val Leu Pro Asp Asn
1               5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Cys Asp Ser Pro Val Leu Pro Asp Asn
1               5

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 10

Cys Asp Gln Pro Val Thr Ala Glu Asn
1               5

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Cys Asp Ser Pro Val Trp Ala Glu Asn
1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Cys Asp Thr Pro Val Leu Ala Glu Asn
1               5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Cys His Asp Arg Pro Val Thr Pro Asp
1               5

<210> SEQ ID NO 14
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Cys Asp Arg Pro Val Thr Pro Asp
1               5

<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Cys Asp Asn Pro Val His Pro Glu
1               5

<210> SEQ ID NO 16
<211> LENGTH: 8
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 16

Cys Asp Val Pro Val Leu Pro Asp
1               5

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Cys Asp Thr Pro Val Tyr Pro Asp
1               5

<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Cys Asp Thr Pro Val Ile Pro Asp
1               5

<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Cys His Asp Arg Pro Val Thr Pro Asp Asn
1               5                   10

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Cys Asp Arg Pro Val Thr Pro Asp Asn
1               5

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Cys Asp Asn Pro Val His Pro Glu Asn
1               5
```

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Cys Asp Val Pro Val Leu Pro Asp Asn
1               5

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Cys Asp Thr Pro Val Tyr Pro Asp Asn
1               5

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Cys Asp Thr Pro Val Ile Pro Asp Asn
1               5

<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Cys Asp Gln Pro Val Leu Pro Asp Gly
1               5

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Cys Asp Met Pro Val Leu Pro Asp Gly
1               5

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 27

Cys Asp Ser Pro Val Leu Pro Asp Gly
1               5

<210> SEQ ID NO 28
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Cys Asp Ser Pro Val Trp Ala Glu Gly
1               5

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Cys Asp Arg Pro Val Ala Pro Glu Gly
1               5

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Cys Asp His Pro Val His Pro Asp Ser
1               5

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Cys Asp Met Pro Val Ser Pro Asp Arg
1               5

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Cys Asp Ser Pro Val Pro Pro Asp Asp
1               5

<210> SEQ ID NO 33
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Cys Asp Gln Pro Val Tyr Pro Asp Ile
1               5

<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Cys Asp Arg Pro Val Tyr Pro Asp Ile
1               5

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Cys Asp His Pro Val Thr Pro Asp Arg
1               5

<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Cys Glu Tyr Pro Val Tyr Pro Glu Ser
1               5

<210> SEQ ID NO 37
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Cys Asp Thr Pro Val Leu Pro Asp Ser
1               5

<210> SEQ ID NO 38
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Cys Asp Met Pro Val Thr Pro Asp Thr
```

```
<210> SEQ ID NO 39
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Cys Asp Ala Pro Val Thr Pro Asp Thr
1               5

<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Cys Asp Ser Pro Val Val Pro Asp Asn
1               5

<210> SEQ ID NO 41
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Cys Asp Leu Pro Val Thr Pro Asp Arg
1               5

<210> SEQ ID NO 42
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Cys Asp Ser Pro Val His Pro Asp Thr
1               5

<210> SEQ ID NO 43
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Cys Asp Ala Pro Val Arg Pro Asp Ser
1               5

<210> SEQ ID NO 44
<211> LENGTH: 9
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 44

Cys Asp Met Pro Val Trp Pro Asp Gly
1               5

<210> SEQ ID NO 45
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Cys Asp Ala Pro Val Tyr Pro Asp Gly
1               5

<210> SEQ ID NO 46
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Cys Asp Arg Pro Val Gln Pro Asp Arg
1               5

<210> SEQ ID NO 47
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Cys Tyr Asp Arg Pro Val Gln Pro Asp Arg
1               5                   10

<210> SEQ ID NO 48
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Cys Asp Met Pro Val Asp Pro Glu Asn
1               5

<210> SEQ ID NO 49
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Cys Asp Met Pro Val Asp Ala Asp Asn
1               5

<210> SEQ ID NO 50

<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Asp Gln Pro Val Leu Pro Asp Cys
1               5

<210> SEQ ID NO 51
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Asp Met Pro Val Leu Pro Asp Cys
1               5

<210> SEQ ID NO 52
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Cys Glu Met Pro Val Asp Pro Asp Asn
1               5

<210> SEQ ID NO 53
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Cys Asp Met Pro Val Asp Pro Asp Asn
1               5

<210> SEQ ID NO 54
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Asp Met Pro Val Asp Pro Asp Asn Cys
1               5

<210> SEQ ID NO 55
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Cys Asp Met Pro Val Asp Pro Gly Ser
1               5

<210> SEQ ID NO 56
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Asp Met Pro Val Asp Pro Gly Ser Cys
1               5

<210> SEQ ID NO 57
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid and may or may not be present
<220> FEATURE:
<221> NAME/KEY: MOD_RES
<222> LOCATION: (2)..(2)
<223> OTHER INFORMATION: Asp or Glu
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (7)..(7)
<223> OTHER INFORMATION: Pro or Ala
<220> FEATURE:
<221> NAME/KEY: MOD_RES
<222> LOCATION: (8)..(8)
<223> OTHER INFORMATION: Asp or Glu
<220> FEATURE:
<221> NAME/KEY: MOD_RES
<222> LOCATION: (9)..(9)
<223> OTHER INFORMATION: Any amino acid and may or may not be present

<400> SEQUENCE: 57

Xaa Xaa Xaa Pro Val Xaa Xaa Xaa Xaa
1               5

<210> SEQ ID NO 58
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 58

His His His His His His
1               5

<210> SEQ ID NO 59
<211> LENGTH: 8
<212> TYPE: PRT
<213> ORGANISM: Artificial Sequence
<220> FEATURE:

```
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cys or not present

<400> SEQUENCE: 59

Xaa Asp Gln Pro Val Leu Pro Asp
1               5

<210> SEQ ID NO 60
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cys or not present

<400> SEQUENCE: 60

Xaa Asp Met Pro Val Leu Pro Asp
1               5

<210> SEQ ID NO 61
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cys or not present

<400> SEQUENCE: 61

Xaa Asp Ser Pro Val Leu Pro Asp
1               5

<210> SEQ ID NO 62
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cys or not present

<400> SEQUENCE: 62

Xaa Asp Ser Pro Val Trp Ala Glu
1               5

<210> SEQ ID NO 63
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cys or not present
```

```
<400> SEQUENCE: 63

Xaa Asp Thr Pro Val Leu Ala Glu
1               5

<210> SEQ ID NO 64
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cys or not present

<400> SEQUENCE: 64

Xaa Asp Gln Pro Val Leu Pro Asp Asn
1               5

<210> SEQ ID NO 65
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cys or not present

<400> SEQUENCE: 65

Xaa Asp Met Pro Val Leu Pro Asp Asn
1               5

<210> SEQ ID NO 66
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cys or not present

<400> SEQUENCE: 66

Xaa Asp Ser Pro Val Leu Pro Asp Asn
1               5

<210> SEQ ID NO 67
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cys or not present

<400> SEQUENCE: 67

Xaa Asp Gln Pro Val Thr Ala Glu Asn
1               5

<210> SEQ ID NO 68
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cys or not present

<400> SEQUENCE: 68

Xaa Asp Ser Pro Val Trp Ala Glu Asn
1               5

<210> SEQ ID NO 69
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cys or not present

<400> SEQUENCE: 69

Xaa Asp Thr Pro Val Leu Ala Glu Asn
1               5

<210> SEQ ID NO 70
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cys or not present

<400> SEQUENCE: 70

Xaa His Asp Arg Pro Val Thr Pro Asp
1               5

<210> SEQ ID NO 71
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cys or not present

<400> SEQUENCE: 71

Xaa Asp Arg Pro Val Thr Pro Asp
1               5

<210> SEQ ID NO 72
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (1)..(1)
<223> OTHER INFORMATION: Cys or not present

<400> SEQUENCE: 72

Xaa Asp Val Pro Val Leu Pro Asp
1               5

<210> SEQ ID NO 73
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cys or not present

<400> SEQUENCE: 73

Xaa Asp Thr Pro Val Tyr Pro Asp
1               5

<210> SEQ ID NO 74
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cys or not present

<400> SEQUENCE: 74

Xaa Asp Thr Pro Val Ile Pro Asp
1               5

<210> SEQ ID NO 75
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cys or not present

<400> SEQUENCE: 75

Xaa His Asp Arg Pro Val Thr Pro Asp Asn
1               5                   10

<210> SEQ ID NO 76
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cys or not present

<400> SEQUENCE: 76

Xaa Asp Arg Pro Val Thr Pro Asp Asn
```

<210> SEQ ID NO 77
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cys or not present

<400> SEQUENCE: 77

Xaa Asp Asn Pro Val His Pro Glu Asn
1               5

<210> SEQ ID NO 78
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cys or not present

<400> SEQUENCE: 78

Xaa Asp Val Pro Val Leu Pro Asp Asn
1               5

<210> SEQ ID NO 79
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cys or not present

<400> SEQUENCE: 79

Xaa Asp Thr Pro Val Tyr Pro Asp Asn
1               5

<210> SEQ ID NO 80
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cys or not present

<400> SEQUENCE: 80

Xaa Asp Thr Pro Val Ile Pro Asp Asn
1               5

<210> SEQ ID NO 81
<211> LENGTH: 9
<212> TYPE: PRT
<213> ORGANISM: Artificial Sequence

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cys or not present

<400> SEQUENCE: 81

Xaa Asp Gln Pro Val Leu Pro Asp Gly
1               5

<210> SEQ ID NO 82
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cys or not present

<400> SEQUENCE: 82

Xaa Asp Met Pro Val Leu Pro Asp Gly
1               5

<210> SEQ ID NO 83
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cys or not present

<400> SEQUENCE: 83

Xaa Asp Ser Pro Val Leu Pro Asp Gly
1               5

<210> SEQ ID NO 84
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cys or not present

<400> SEQUENCE: 84

Xaa Asp Ser Pro Val Trp Ala Glu Gly
1               5

<210> SEQ ID NO 85
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cys or not present
```

```
<400> SEQUENCE: 85

Xaa Asp Arg Pro Val Ala Pro Glu Gly
1               5

<210> SEQ ID NO 86
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cys or not present

<400> SEQUENCE: 86

Xaa Asp His Pro Val His Pro Asp Ser
1               5

<210> SEQ ID NO 87
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cys or not present

<400> SEQUENCE: 87

Xaa Asp Met Pro Val Ser Pro Asp Arg
1               5

<210> SEQ ID NO 88
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cys or not present

<400> SEQUENCE: 88

Xaa Asp Ser Pro Val Pro Pro Asp Asp
1               5

<210> SEQ ID NO 89
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cys or not present

<400> SEQUENCE: 89

Xaa Asp Gln Pro Val Tyr Pro Asp Ile
1               5
```

```
<210> SEQ ID NO 90
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cys or not present

<400> SEQUENCE: 90

Xaa Asp Arg Pro Val Tyr Pro Asp Ile
1               5

<210> SEQ ID NO 91
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cys or not present

<400> SEQUENCE: 91

Xaa Asp His Pro Val Thr Pro Asp Arg
1               5

<210> SEQ ID NO 92
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cys or not present

<400> SEQUENCE: 92

Xaa Glu Tyr Pro Val Tyr Pro Glu Ser
1               5

<210> SEQ ID NO 93
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cys or not present

<400> SEQUENCE: 93

Xaa Asp Thr Pro Val Leu Pro Asp Ser
1               5

<210> SEQ ID NO 94
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (1)..(1)
<223> OTHER INFORMATION: Cys or not present

<400> SEQUENCE: 94

Xaa Asp Met Pro Val Thr Pro Asp Thr
1               5

<210> SEQ ID NO 95
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cys or not present

<400> SEQUENCE: 95

Xaa Asp Ala Pro Val Thr Pro Asp Thr
1               5

<210> SEQ ID NO 96
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cys or not present

<400> SEQUENCE: 96

Xaa Asp Ser Pro Val Val Pro Asp Asn
1               5

<210> SEQ ID NO 97
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cys or not present

<400> SEQUENCE: 97

Xaa Asp Leu Pro Val Thr Pro Asp Arg
1               5

<210> SEQ ID NO 98
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cys or not present

<400> SEQUENCE: 98
```

Xaa Asp Ser Pro Val His Pro Asp Thr
1               5

<210> SEQ ID NO 99
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cys or not present

<400> SEQUENCE: 99

Xaa Asp Ala Pro Val Arg Pro Asp Ser
1               5

<210> SEQ ID NO 100
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cys or not present

<400> SEQUENCE: 100

Xaa Asp Met Pro Val Trp Pro Asp Gly
1               5

<210> SEQ ID NO 101
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cys or not present

<400> SEQUENCE: 101

Xaa Asp Ala Pro Val Tyr Pro Asp Gly
1               5

<210> SEQ ID NO 102
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cys or not present

<400> SEQUENCE: 102

Xaa Asp Arg Pro Val Gln Pro Asp Arg
1               5

<210> SEQ ID NO 103
<211> LENGTH: 10
<212> TYPE: PRT

<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cys or not present

<400> SEQUENCE: 103

Xaa Tyr Asp Arg Pro Val Gln Pro Asp Arg
1               5                   10

<210> SEQ ID NO 104
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cys or not present

<400> SEQUENCE: 104

Xaa Asp Met Pro Val Asp Pro Glu Asn
1               5

<210> SEQ ID NO 105
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cys or not present

<400> SEQUENCE: 105

Xaa Asp Met Pro Val Asp Ala Asp Asn
1               5

<210> SEQ ID NO 106
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Cys or not present

<400> SEQUENCE: 106

Asp Gln Pro Val Leu Pro Asp Xaa
1               5

<210> SEQ ID NO 107
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)

<223> OTHER INFORMATION: Cys or not present

<400> SEQUENCE: 107

Asp Met Pro Val Leu Pro Asp Xaa
1               5

<210> SEQ ID NO 108
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cys or not present

<400> SEQUENCE: 108

Xaa Glu Met Pro Val Asp Pro Asp Asn
1               5

<210> SEQ ID NO 109
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cys or not present

<400> SEQUENCE: 109

Xaa Asp Asn Pro Val His Pro Glu
1               5

<210> SEQ ID NO 110
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Asp Gln Pro Val Leu Pro Asp
1               5

<210> SEQ ID NO 111
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Asp Met Pro Val Leu Pro Asp
1               5

<210> SEQ ID NO 112
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 112

Asp Ser Pro Val Leu Pro Asp
1               5

<210> SEQ ID NO 113
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Asp Ser Pro Val Trp Ala Glu
1               5

<210> SEQ ID NO 114
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Asp Thr Pro Val Leu Ala Glu
1               5

<210> SEQ ID NO 115
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Asp Gln Pro Val Leu Pro Asp Asn
1               5

<210> SEQ ID NO 116
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Asp Met Pro Val Leu Pro Asp Asn
1               5

<210> SEQ ID NO 117
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Asp Ser Pro Val Leu Pro Asp Asn
1               5

<210> SEQ ID NO 118
<211> LENGTH: 8
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Asp Gln Pro Val Thr Ala Glu Asn
1               5

<210> SEQ ID NO 119
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Asp Ser Pro Val Trp Ala Glu Asn
1               5

<210> SEQ ID NO 120
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Asp Thr Pro Val Leu Ala Glu Asn
1               5

<210> SEQ ID NO 121
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

His Asp Arg Pro Val Thr Pro Asp
1               5

<210> SEQ ID NO 122
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Asp Arg Pro Val Thr Pro Asp
1               5

<210> SEQ ID NO 123
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Asp Val Pro Val Leu Pro Asp
```

```
1               5
```

<210> SEQ ID NO 124
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

```
Asp Thr Pro Val Tyr Pro Asp
1               5
```

<210> SEQ ID NO 125
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

```
Asp Thr Pro Val Ile Pro Asp
1               5
```

<210> SEQ ID NO 126
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

```
His Asp Arg Pro Val Thr Pro Asp Asn
1               5
```

<210> SEQ ID NO 127
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

```
Asp Arg Pro Val Thr Pro Asp Asn
1               5
```

<210> SEQ ID NO 128
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

```
Asp Asn Pro Val His Pro Glu Asn
1               5
```

<210> SEQ ID NO 129
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 129

Asp Val Pro Val Leu Pro Asp Asn
1               5

<210> SEQ ID NO 130
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Asp Thr Pro Val Tyr Pro Asp Asn
1               5

<210> SEQ ID NO 131
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Asp Thr Pro Val Ile Pro Asp Asn
1               5

<210> SEQ ID NO 132
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Asp Gln Pro Val Leu Pro Asp Gly
1               5

<210> SEQ ID NO 133
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Asp Met Pro Val Leu Pro Asp Gly
1               5

<210> SEQ ID NO 134
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Asp Ser Pro Val Leu Pro Asp Gly
1               5

<210> SEQ ID NO 135

```
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Asp Ser Pro Val Trp Ala Glu Gly
1               5

<210> SEQ ID NO 136
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Asp Arg Pro Val Ala Pro Glu Gly
1               5

<210> SEQ ID NO 137
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Asp His Pro Val His Pro Asp Ser
1               5

<210> SEQ ID NO 138
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Asp Met Pro Val Ser Pro Asp Arg
1               5

<210> SEQ ID NO 139
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Asp Ser Pro Val Pro Pro Asp Asp
1               5

<210> SEQ ID NO 140
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140
```

```
Asp Gln Pro Val Tyr Pro Asp Ile
1               5

<210> SEQ ID NO 141
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Asp Arg Pro Val Tyr Pro Asp Ile
1               5

<210> SEQ ID NO 142
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Asp His Pro Val Thr Pro Asp Arg
1               5

<210> SEQ ID NO 143
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Glu Tyr Pro Val Tyr Pro Glu Ser
1               5

<210> SEQ ID NO 144
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Asp Thr Pro Val Leu Pro Asp Ser
1               5

<210> SEQ ID NO 145
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Asp Met Pro Val Thr Pro Asp Thr
1               5

<210> SEQ ID NO 146
<211> LENGTH: 8
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 146

Asp Ala Pro Val Thr Pro Asp Thr
1               5

<210> SEQ ID NO 147
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Asp Ser Pro Val Val Pro Asp Asn
1               5

<210> SEQ ID NO 148
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Asp Leu Pro Val Thr Pro Asp Arg
1               5

<210> SEQ ID NO 149
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Asp Ser Pro Val His Pro Asp Thr
1               5

<210> SEQ ID NO 150
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Asp Ala Pro Val Arg Pro Asp Ser
1               5

<210> SEQ ID NO 151
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Asp Met Pro Val Trp Pro Asp Gly
1               5
```

```
<210> SEQ ID NO 152
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Asp Ala Pro Val Tyr Pro Asp Gly
1               5

<210> SEQ ID NO 153
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Asp Arg Pro Val Gln Pro Asp Arg
1               5

<210> SEQ ID NO 154
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Tyr Asp Arg Pro Val Gln Pro Asp Arg
1               5

<210> SEQ ID NO 155
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Asp Met Pro Val Asp Pro Glu Asn
1               5

<210> SEQ ID NO 156
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Asp Met Pro Val Asp Ala Asp Asn
1               5

<210> SEQ ID NO 157
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157
```

```
Glu Met Pro Val Asp Pro Asp Asn
1               5

<210> SEQ ID NO 158
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Asp Asn Pro Val His Pro Glu
1               5

<210> SEQ ID NO 159
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cys or not present

<400> SEQUENCE: 159

Cys Asp Met Pro Val Asp Pro Asp Asn
1               5
```